United States Patent [19]

Barbacid

[11] Patent Number: 5,348,864
[45] Date of Patent: Sep. 20, 1994

[54] MOUSE VAV PROTO-ONCOGENE DNA AND PROTEIN SEQUENCES

[75] Inventor: Mariano Barbacid, Lawrenceville, N.J.

[73] Assignee: E. R. Squibb & Sons, Inc., Princeton, N.J.

[21] Appl. No.: 646,537

[22] Filed: Jan. 25, 1991

[51] Int. Cl.$^5$ .................. C12P 21/06; C12N 5/00; C12N 15/70; C07K 13/00
[52] U.S. Cl. .................. 435/69.1; 435/320.1; 435/252.3; 435/240.2; 435/6; 435/70.1; 435/70.3; 435/91.1; 435/172.3; 536/22.1; 536/23.1; 536/23.5; 530/350; 935/1; 935/23; 935/29; 935/25; 935/74
[58] Field of Search .............. 435/6, 240.2, 320.1, 435/69.1, 252.3, 91, 70.1, 70.3, 172.3, 91.1; 536/27, 28, 29, 22.1, 23.1, 25.4, 23.5; 530/350

[56] References Cited

U.S. PATENT DOCUMENTS 4,394,443 7/1983 Weisman et al. .................. 435/6

FOREIGN PATENT DOCUMENTS

WO8910412 4/1989 PCT Int'l Appl. .
WO9014440 5/1990 PCT Int'l Appl. .

OTHER PUBLICATIONS

Katzav, S. et al., Embo Journal 8, 2283–2290 (1989) "Vav, a novel human oncogene derived from a locus ubiquitously expressed in hematopoietic cells".
Barbacid, M., Immunol. Series 41, 121–148 (1988) "*ras* Oncogenes in Human and Carcinogen–Induced Animal Tumors".

*Primary Examiner*—Margaret Parr
*Assistant Examiner*—Miguel Escallon

[57] ABSTRACT

Nucleic acid sequences, particularly DNA sequences, coding for all or part of a vav mouse proto-oncogene protein or for a modified vav mouse proto-oncogene protein, expression vectors containing the DNA sequences, host cells containing the expression vectors, and methods utilizing these materials. The invention also concerns polypeptide molecules comprising all or part of a vav mouse proto-oncogene protein or a modified vav mouse proto-oncogene protein, and methods for producing these polypeptide molecules.

11 Claims, 12 Drawing Sheets

FIG. 2A

```
 1  GCCGGCAGCCACC                                                                                     13

ATGGAGCTCTGGGACAGTGCACCCACTGGCTGATCCAGTGTCGGGTGCTCCCAGC                                           73
 1   M  E  L  W  R  Q  C  T  H  W  L  I  Q  C  R  V  L  P  P  S

CACCCGTGTGACCTGGGAGGGGGCCCAGGTGTGTGAGCTGGCACAGGCACTGCGGGACGGT                                    133
21   H  R  V  T  W  E  G  A  Q  V  C  E  L  A  Q  A  L  R  D  G

GTCCTCTTGTGCCAATTGCTTAACAACCTGCTTCCCCAGGCCATTAATCTTCGCGAGGTT                                    193
41   V  L  L  C  Q  L  L  N  N  L  L  P  Q  A  I  N  L  R  E  V

AACTTGCGGCCCCAGATGTCCCAGTTCCTTTGTCTTAAGAACATTCGAACCTTCCTGTCT                                    253
61   N  L  R  P  Q  M  S  Q  F  L  C  L  K  N  I  R  T  F  L  S

ACTTGCTGTGAGAAGTTCGGCCTCAAGCGGAGTGAACTCTTTGAGGCTTTTGACCTCTTC                                    313
81   T  C  C  E  K  F  G  L  K  R  S  E  L  F  E  A  F  D  L  F

GATGTGCAGGACTTTGGAAAGGTCATCTACACCCTGTCTGCTCTGTCATGGACACCCATT                                    373
101  D  V  Q  D  F  G  K  V  I  Y  T  L  S  A  L  S  W  T  P  I
```

FIG.2B

```
121  GCCCAGAACAAAGGAATCATGCCCTTCCCAACAGAGGACAGCGCTCTGAACGACGAAGAT    433
      A  Q  N  K  G  I  M  P  F  P  T  E  D  S  A  L  N  D  E  D
141  ATTTACAGTGGCCTTTCAGACCAGATTGATGACACCGCAGAAGAAGACGAGGACCTTTAT    493
      I  Y  S  G  L  S  D  Q  I  D  D  T  A  E  E  D  E  D  L  Y
161  GACTGCGTGGAAAATGAGGAGGGGGACGAGATCTACGAGGACCTAATGCGCTTG         553
      D  C  V  E  N  E  A  E  G  D  E  I  Y  E  D  L  M  R  L
181  GAGTCGGTGCCTACGCCACCCAAGATGACAGAGTATGATAAGCGCTGCTGCCTGCGG      613
      E  S  V  P  T  P  P  K  M  T  E  Y  D  K  R  C  C  L  R
201  GAGATCCAGCAGACGGAGGAGAAGTATACAGACACACTGGGCTCCATCCAGCAGCACTTC   673
      E  I  Q  Q  T  E  E  K  Y  T  D  T  L  G  S  I  Q  Q  H  F
221  ATGAAGCCTCTGCAGCGATTCCTTAAGCCTCAAGACATGGAGACCATCTTTGTCAACATT   733
      M  K  P  L  Q  R  F  L  K  P  Q  D  M  E  T  I  F  V  N  I
241  GAGGAGCTGTTCTCTGTGCATACCCACTTCTTAAAGGAACTGAAGGATGCCCTGGCTGGC   793
      E  E  L  F  S  V  H  T  H  F  L  K  E  L  K  D  A  L  A  G
261  CCGGGGAGCAACAACACTGTATCAGGTCTTCATCAAGTACAAGGAGAGGTTCCTGGTTTAT  853
      P  G  A  T  T  L  Y  Q  V  F  I  K  Y  K  E  R  F  L  V  Y
281  GGCCGTTATTGCAGTCAGGTGGAGTCAGCAAGCACTTGGATCAAGTGGCCACAGCA      913
      G  R  Y  C  S  Q  V  E  S  A  S  K  H  L  D  Q  V  A  T  A
```

FIG.2C

```
301 CGGGAGGATGTGCAGATGAAGCTGGAGGAATGTTCTCAAAGAGCTAACAATGGCCGATTC    973
     R  E  D  V  Q  M  K  L  E  E  C  S  Q  R  A  N  N  G  R  F

321 ACCCTACGGTCTGCTGATGGTACCTATGCAGCGGGTGCTGAAGTACCACCTCCTTCTCCA   1033
     T  L  R  S  A  D  G  T  Y  A  A  G  A  E  V  P  P  P  S  P

341 GGAGCTAGTGAAACACACAGGATGCTACAGAGAAGGAGAACTGCGGTTGGCCCTGGAC    1093
     G  A  S  E  T  H  T  G  C  Y  R  E  G  E  L  R  L  A  L  D

361 GCCATGAGGGACCTGGCACAGTGCGTGAACGAGGTCAAGAGGGACAATGAAACCCTACGG   1153
     A  M  R  D  L  A  Q  C  V  N  E  V  K  R  D  N  E  T  L  R

381 CAGATCACAAACTTTCAGCTGTCCATTGAGAACCTGGACCAGTCTCTGGCTAACTATGGC   1213
     Q  I  T  N  F  Q  L  S  I  E  N  L  D  Q  S  L  A  N  Y  G

401 CGGCCCAAGATTGACGGTGAGCTCAAGATTACCTCAGTGGAGCGTCGCTCAAAGACAGAC   1273
     R  P  K  I  D  G  E  L  K  I  T  S  V  E  R  R  S  K  T  D

421 AGGTATGCCTTCCTGCTGGACAAAGCACTGCTCATCTGTAAACGCCGGGGACTCTTAC    1333
     R  Y  A  F  L  L  D  K  A  L  L  I  C  K  R  R  G  D  S  Y

441 GACCTCAAAGCCTCGGTGAACTTGCACAGTTCCAAGTTCCAGTTTCAGATGACTCCTCCGGGGAG   1393
     D  L  K  A  S  V  N  L  H  S  F  Q  V  S  D  D  D  S  S  G  E
```

FIG.2D

```
     CGAGACAACAAGAAGTGGAGCCATATGTTCCTTCTGATTGAGGATCAAGGGCCCCAGGGC  1453
461  R  D  N  K  K  W  S  H  M  F  L  L  I  E  D  Q  G  A  Q  G

TATGAGCTGTTCTTCAAGACTCGGGAGCTGAAGAAGAAGTGGATGGAACAGTTCGAAATG  1513
481  Y  E  L  F  F  K  T  R  E  L  K  K  K  W  M  E  Q  F  E  M

GCCATCTCCAACATTTACCCAGAGAATGCTACAGCCAATGGGCATGATTTTCAGATGTTC  1573
501  A  I  S  N  I  Y  P  E  N  A  T  A  N  G  H  D  F  Q  M  F

TCCTTTGAGGAGACCACTTCCTGCAAGGCCTGCCAGATGTTACTCAGAGGCACATTCTAC  1633
521  S  F  E  E  T  T  S  C  K  A  C  Q  M  L  L  R  G  T  F  Y

CAGGGATATCGCTGTGTTACAGGTGCGGGCACCTGCACACAAGGAGTGTCTGGGGAGAGTG  1693
541  Q  G  Y  R  C  V  T  G  R  A  P  A  H  K  E  C  L  G  R  V

CCTCCCCCTTGTCGCCATGGGCAAGATTTCGCAGGAACCATGAAGAAGAAGGACAAGCTCCAT  1753
561  P  P  P  C  R  H  G  Q  D  F  A  G  T  M  K  K  K  D  K  L  H

CGAAGGGCCCAGGACAAGAAAAGGAATGAATTGGGTCTGCCTAAGATGGAAGTGTTTCAG  1813
581  R  R  A  Q  D  K  K  R  N  E  L  G  L  P  K  M  E  V  F  Q

GAATACTATGGGATCCCCCCACCTGGAGCCTTTGGCCCATTTTTACGGCTCAACCCT  1873
601  E  Y  Y  G  I  P  P  P  P  G  A  F  G  P  F  L  R  L  N  P

GGGGACATTGTGGAGCTCACTAAGGCAGAGGCTGAGCACAACTGGTGGGAGGGAAGGAAT  1933
621  G  D  I  V  E  L  T  K  A  E  A  E  H  N  W  W  E  G  R  N
```

FIG.2E

```
641  ACTGCTACAAATGAAGTCGGGTTCCCTGTAACAGAGTGCATCCCTATGTCCACGGC  1993
      T  A  T  N  E  V  G  W  F  P  C  N  R  V  H  P  Y  V  H  G
661  CCTCCTCAGGACCTGTCTGTGCATCTCTGGTATGCGGGCCCTATGGAACGAGCAGGCGCT  2053
      P  P  Q  D  L  S  V  H  L  W  Y  A  G  P  M  E  R  A  G  A
681  GAGGGCATCCTCACCAACCGTTCTGATGGGACCTATCTGGTGCGCCAGAGGGTGAAAGAT  2113
      E  G  I  L  T  N  R  S  D  G  T  Y  L  V  R  Q  R  V  K  D
701  ACAGCGGAGTTCGCCATCAGCATTAAGTATAACGTGGAGGTCAAGCATATTAAAATCATG  2173
      T  A  E  F  A  I  S  I  K  Y  N  V  E  V  K  H  I  K  I  M
721  ACGTCAGAGGGTTGTACCGGATCACAGAGAAGAAGGCTTTCCGGGGCCTTCTGGAACTG  2233
      T  S  E  G  L  Y  R  I  T  E  K  K  A  F  R  G  L  L  E  L
741  GTAGAGTTTTATCAGCAGAATTCCCTCAAAGATTGCTTCAAGTCGTTGGACACCACCTTG  2293
      V  E  F  Y  Q  Q  N  S  L  K  D  C  F  K  S  L  D  T  T  L
761  CAGTTTCCTTATAAGGAACCTGAGAGGAGAGCCATCAGCAAGCCACCAGCTGGAAGCACC  2353
      Q  F  P  Y  K  E  P  E  R  R  A  I  S  K  P  P  A  G  S  T
```

MOUSE VAV PROTO-ONCOGENE DNA AND PROTEIN SEQUENCES

BACKGROUND OF THE INVENTION

Oncogenic activation has proven to be a valuable genetic marker for the identification of novel vertebrate genes [Varmus, H., Science 240, 1427–1435 (1988)]. The ras gene family, certain tyrosine protein kinases (src gene family, abl, trk, met, ret) and transcription factors (fos, jun, erbA) are just some of the best known examples. Although the precise function of these genes remains to be elucidated, their capacity to induce neoplasia strongly suggests that they play critical roles in the control of signal transduction processes [Bishop, J. M., Science 235, 305–311 ( 1987 )].

The property of oncogenic activation has been used to isolate a number of novel human genes, one of which (vav) has been recently characterized at the molecular level. The ray gene was first identified when it became activated as an oncogene by a fortuitous rearrangement during the course of gene transfer assays [Katzav, S. et al., EMBO J. 8, 2283–2290 (1989)]. Molecular characterization of the human vav oncogene revealed a molecule capable of coding for a 797 amino acid polypeptide whose amino-terminus had been replaced by spurious sequences derived from the bacterial Tn5 gene used to confer G418 resistance to the transfected cells [Katzav, S. et al., supra]. The rest of the vav oncogene product contains a series of structural motifs reminiscent of those found in certain transcription factors, including a highly acidic amino-terminal region and a cystein-rich domain that depicts two putative metal binding structures [Johnson, P. F. et al., Annu. Rev. Biochem. 58, 799–839 (1989)].

The most intriguing feature of the vav gene is its pattern of expression. Analysis of ray gene transcripts in a series of human cell lines indicated that the vav gene is specifically expressed in cells of hematopoietic origin [Katzav, S. et al., supra]. No vav gene expression could be observed in either epithelial, mesenchymal or neuroectodermal cells. Interestingly, lymphoid, myeloid and erythroid cell lines contained comparable levels of vav gene transcripts. Similar results were obtained when normal human cells were examined, including B and T lymphocytes, macrophages and platelets [Katzav, S. et al., supra]. These observations suggest that the vav gene may play a basic role in hematopoiesis that is not influenced by differentiation programs.

It would be useful to isolate oncogenes from other mammalian species related to the human vav oncogene in order to more easily study the role of this protein in oncogenesis.

SUMMARY OF THE INVENTION

The present invention concerns an isolated nucleic acid molecule comprising a nucleic acid sequence coding for all or part of a mouse vav proto-oncogene protein. Preferably, the nucleic acid molecule is a DNA (deoxyribonucleic acid) molecule, and the nucleic acid sequence is a DNA sequence. Further preferred is a DNA sequence having all or part of the nucleotide sequence substantially as shown in FIG. 2 [SEQ. ID NO: 1].

The present invention further concerns expression vectors comprising a DNA sequence coding for all or part of a mouse vav proto-oncogene protein.

The present invention additionally concerns prokaryotic or eukaryotic host cells containing an expression vector which comprises a DNA sequence coding for all or part of a mouse vav proto-oncogene protein.

The present invention also concerns methods for detecting nucleic acid sequences coding for all or part of a mouse vav proto-oncogene protein or related nucleic acid sequences.

The present invention further concerns polypeptide molecules comprising all or part of a mouse vav proto-oncogene protein.

DETAILED DESCRIPTION OF THE INVENTION

Figure 2F:
FIG. 2 shows the nucleotide [SEQ. ID NO: 1] and deduced amino acid [SEQ. ID NO: 2] sequence of the 2793 bp insert of pMB24. The sequences of the flanking EcoRI linkers have been omitted. Numbers to the right of the sequence indicate nucleotide numbers and those to the left amino acid numbers. Underlined sequences correspond to those structures highlighted in (A). The cystein-rich domain has been boxed. Cysteine and histidine residues corresponding to the putative zinc finger-like structures (Cys-$X_2$-Cys-$X_{13}$-Cys-$X_2$-Cys [SEQ. ID. NO.: 4] and His-$X_2$-Cys-$X_6$-Cys-$X_2$-His [SEQ. ID. NO.: 4]) have been shaded. A putative protein kinase A phospho-rylation site is underlined by a crosshatched box and a putative polyadenylation signal by a wavy line.

The present invention concerns an isolated nucleic acid molecule comprising a nucleic acid sequence coding for all or part of a mouse vav proto-oncogene protein. Preferably, the nucleic acid molecule is a DNA molecule and the nucleic acid sequence is a DNA sequence. Further preferred is a DNA sequence having all or part of the nucleotide sequence substantially as shown in FIG. 2 [SEQ. ID NO: 1], or a DNA sequence complementary to this DNA sequence. In the case of a nucleotide sequence (e.g., a DNA sequence) coding for part of a mouse vav proto-oncogene protein, it is preferred that the nucleotide sequence be at least about 15 nucleotides in length.

The DNA sequences of the present invention can be isolated from a variety of sources, although the presently preferred sequence has been isolated from two different mouse cDNA libraries. The exact amino acid sequence of the polypeptide molecule produced will vary with the initial DNA sequence.

The DNA sequences of the present invention can be obtained using various methods well-known to those of ordinary skill in the art. At least three alternative principal methods may be employed:

(1) the isolation of a double-stranded DNA sequence from genomic DNA or complementary DNA (cDNA) which contains the sequence;
(2) the chemical synthesis of the DNA sequence; and
(3) the synthesis of the DNA sequence by polymerase chain reaction (PCR).

In the first approach, a genomic or cDNA library can be screened in order to identify a DNA sequence coding for all or part of a mouse vav proto-oncogene protein. For example, a mouse cDNA library can be screened in order to identify a DNA sequence coding for all or part of a mouse vav proto-oncogene protein. Various mouse cDNA libraries, for example, those derived from WEHI-3 (ATCC. TIB 68) cells and those derived from EL-4 (ATCC. TIB 39) cells can be employed. Various techniques can be used to screen the genomic DNA or cDNA libraries.

For example, labeled single stranded DNA probe sequences duplicating a sequence present in the target genomic DNA or cDNA coding for all or part of a mouse ray proto-oncogene protein can be employed in DNA/DNA hybridization procedures carried out on cloned copies of the genomic DNA or cDNA which have been denatured to single stranded form.

A genomic DNA or cDNA library can also be screened for a genomic DNA or cDNA coding for all or part of a mouse vav proto-oncogene protein using immunoblotting techniques.

In one typical screening method suitable for either immunoblotting or hybridization techniques, the genomic DNA library, which is usually contained in a vector such as λGT11, or cDNA library is first spread out on agarose plates, and then the clones are transferred to filter membranes, for example, nitrocellulose membranes. A DNA probe can then be hybridized or an antibody can then be bound to the clones to identify those clones containing the genomic DNA or cDNA coding for all or part of a mouse vav proto-oncogene protein.

In the second approach, the DNA sequence of the present invention coding for all or part of a mouse vav proto-oncogene protein can be chemically synthesized. For example, the DNA sequence coding for a mouse vav proto-oncogene protein can be synthesized as a series of 100 base oligonucleotides that can then be sequentially ligated (via appropriate terminal restriction sites) so as to form the correct linear sequence of nucleotides.

In the third approach, the DNA sequences of the present invention coding for all or part of a mouse vav proto-oncogene protein can be synthesized using PCR. Briefly, pairs of synthetic DNA oligonucleotides at least 15 bases in length (PCR primers) that hybridize to opposite strands of the target DNA sequence are used to enzymatically amplify the intervening region of DNA on the target sequence. Repeated cycles of heat denaturation of the template, annealing of the primers and extension of the 3'-termini of the annealed primers with a DNA polymerase results in amplification of the segment defined by the 5' ends of the PCR primers. See, U.S. Pat. Nos. 4,683,195 and 4,683,202.

The DNA sequences of the present invention can be used in a variety of ways in accordance with the present invention. For example, they can be used as DNA probes to screen other cDNA and genomic DNA libraries so as to select by hybridization other DNA sequences that code for proteins related to a mouse vav proto-oncogene protein. In addition, the DNA sequences of the present invention coding for all or part of a mouse vav proto-oncogene protein can be used as DNA probes to screen other cDNA and genomic DNA libraries to select by hybridization DNA sequences that code for the vav proto-oncogene protein molecules from organisms other than mice.

The DNA sequences of the present invention coding for all or part of a mouse vav proto-oncogene protein can also be modified (i.e., mutated) to prepare various mutations. Such mutations may be either degenerate, i.e., the mutation does not change the amino acid sequence encoded by the mutated codon, or non-degenerate, i.e., the mutation changes the amino acid sequence encoded by the mutated codon. These modified DNA sequences may be prepared, for example, by mutating a mouse vav proto-oncogene protein DNA sequence so that the mutation results in the deletion, substitution, insertion, inversion or addition of one or more amino acids in the encoded polypeptide using various methods known in the art. For example, the methods of site-directed mutagenesis described in Taylor, J. W. et al., Nucl. Acids Res. 13, 8749–8764 (1985) and Kunkel, J. A., Proc. Natl. Acad. Sci. USA 82, 482–492 (1985) may be employed. In addition, kits for site-directed mutagenesis may be purchased from commercial vendors. For example, a kit for performing site-directed mutagenesis may be purchased from Amersham Corp. (Arlington Heights, Ill.). Both degenerate and non-degenerate mutations may be advantageous in producing or using the polypeptides of the present invention. For example, these mutations may permit higher levels of production, easier purification, or provide additional restriction endonuclease recognition sites. All such modified DNAs (and the encoded polypeptide molecules) are included within the scope of the present invention.

As used in the present application, the term "modified", when referring to a nucleotide or polypeptide sequence, means a nucleotide or polypeptide sequence which differs from the wild-type sequence found in nature.

The present invention further concerns expression vectors comprising a DNA sequence coding for all or part of a mouse vav proto-oncogene protein. The expression vectors preferably contain all or part of the DNA sequence having the nucleotide sequence substantially as shown in FIG. 2 [SEQ. ID NO: 1]. Further preferred are expression vectors comprising one or more regulatory DNA sequences operatively linked to the DNA sequence coding for all or part of a mouse vav proto-oncogene protein. As used in this context, the term "operatively linked" means that the regulatory DNA sequences are capable of directing the replication and/or the expression of the DNA sequence coding for all or part of a mouse vav proto-oncogene protein.

Expression vectors of utility in the present invention are often in the form of "plasmids", which refer to circular double stranded DNAs which, in their vector form, are not bound to the chromosome. However, the invention is intended to include such other forms of expression vectors which serve equivalent functions and which become known in the art subsequently hereto.

Expression vectors useful in the present invention typically contain an origin of replication, a promoter located in front of (i.e., upstream of) the DNA sequence and followed by the DNA sequence coding for all or part of a mouse vav proto-oncogene protein, transcription termination sequences and the remaining vector. The expression vectors may also include other DNA sequences known in the art, for example, stability leader sequences which provide for stability of the expression product, secretory leader sequences which provide for secretion of the expression product, sequences which allow expression of the structural gene to be modulated (e.g., by the presence or absence of nutrients or other inducers in the growth medium), marking sequences which are capable of providing phenotypic selection in transformed host cells, and sequences which provide sites for cleavage by restriction endonucleases. The characteristics of the actual expression vector used must be compatible with the host cell which is to be employed. For example, when cloning in a mammalian cell system, the expression vector should contain promoters isolated from the genome of mammalian cells, (e.g., mouse metallothionien promoter), or from viruses that grow in these cells (e.g., vaccinia virus 7.5 K promoter). An expression vector as contemplated by the present invention is at least capable of directing the replication, and preferably the expression, of the DNA sequences of the present invention. Suitable origins of replication include, for example, the Ori origin of replication from the ColE1 derivative of pMB1. Suitable promoters include, for example, the long terminal repeats of the Moloney sarcoma virus, the Rous sarcoma virus and the mouse mammary tumor virus, as well as the early regions of Simian virus 40 and the polyoma virus. As selectable markers, the bacterial genes encoding resistance to the antibodies neomycin and G418 (neo) puromycin (put) or hygromycin (hygro), or mammalian genes encoding thymidine kinase can be employed. All of these materials are known in the art and are commercially available.

Particularly preferred is the expression vector designated pMB24, described herein below, which contains the DNA sequence coding for a mouse vav proto-oncogene protein, or expression vectors with the identifying characteristics of pMB24.

E. coli host cells (strain XL1-Blue) containing the plasmid pMB24 were deposited with the American Type Culture Collection, Rockville, Md. on Jan. 23, 1991 under the Budapest Treaty and assigned ATCC. accession no. 68516. pMB24 contains a cDNA clone of the mouse vav proto-oncogene encompassing the entire coding sequence.

Suitable expression vectors containing the desired coding and control sequences may be constructed using standard recombinant DNA techniques known in the art, many of which are described in Maniatis, T. et al., *Molecular Cloning: A Laboratory Manual*, Cold Spring Harbor Laboratory, Cold Spring Harbor, N.Y. (1982).

The present invention additionally concerns host cells containing an expression vector which comprises a DNA sequence coding for all or part of a mouse vav proto-oncogene protein. The host cells preferably contain an expression vector which comprises all or part of the DNA sequence having the nucleotide sequence substantially as shown in FIG. 2 [SEQ. ID NO: 1]. Further preferred are host cells containing an expression vector comprising one or more regulatory DNA sequences capable of directing the replication and/or the expression of and operatively linked to a DNA sequence coding for all or part of a mouse vav proto-oncogene protein. Suitable host cells include both prokaryotic and eukaryotic cells. Suitable prokaryotic host cells include, for example, various strains of E. coli such as DH5, C600 and LL1. Suitable eukaryotic host cells include, for example, mouse NIH3T3 and BALB3T3 cells, rat Rat-2 cells, monkey COS cells, human Hela cells and hamster CHO cells.

Preferred as host cells are mouse NIH3T3 cells.

Expression vectors may be introduced into host cells by various methods known in the art. For example, transfection of host cells with expression vectors can be carried out by the calcium phosphate precipitation method. However, other methods for introducing expression vectors into host cells, for example, electroporation, biolistic fusion, liposomal fusion, nuclear injection and viral or phage infection can also be employed.

Once an expression vector has been introduced into an appropriate host cell, the host cell can be cultured under conditions permitting expression of large amounts of the desired polypeptide, in this case a polypeptide molecule comprising all or part of a mouse vav proto-oncogene protein. Such polypeptides are useful in the study of the characteristics of a mouse vav proto-oncogene protein, for example, its role in oncogenesis. Such polypeptides can also be used to identify potential anti-cancer drugs. For example, a compound which is able to bind to or inhibit the function of the vav proto-oncogene may be an effective cancer chemotherapeutic agent.

Host cells containing an expression vector which contains a DNA sequence coding for all or part of a mouse vav proto-oncogene protein may be identified by one or more of the following four general approaches: (a) DNA-DNA hybridizaiton; (b) the presence or absence of marker gene functions; (c) assessing the level of transcription as measured by the production of mouse vav proto-oncogene protein mRNA transcripts in the host cell; and (d) detection of the gene product immunologically.

In the first approach, the presence of a DNA sequence coding for all or part of a mouse ray proto-oncogene protein can be detected by DNA-DNA or RNA-DNA hybridization using probes complementary to the DNA sequence.

In the second approach, the recombinant expression vector host system can be identified and selected based upon the presence or absence of certain marker gene function (e.g., thymidine kinase activity, resistance to antibiotics, etc.). A marker gene can be placed in the same plasmid as the DNA sequence coding for all or part of a mouse vav proto-oncogene protein under the regulation of the same or a different promoter used to regulate a mouse vav proto-oncogene protein coding sequence. Expression of the marker gene in response to induction or selection indicates expression of the DNA sequence coding for all or part of a mouse ray proto-oncogene protein.

In the third approach, the production of mouse vav proto-oncogene protein mRNA transcripts can be assessed by hybridization assays. For example, polyadenylated RNA can be isolated and analyzed by Northern blotting or nuclease protection assay using a probe complementary to the RNA sequence. Alternatively, the total nucleic acids of the host cell may be extracted and assayed for hybridization to such probes.

In the fourth approach, the expression of all or part of a mouse vav proto-oncogene protein can be assessed immunologically, for example, by Western blotting.

The DNA sequences of expression vectors, plasmids or DNA molecules of the present invention may be determined by various methods known in the art. For example, the dideoxy chain termination method as described in Sanger et al., Proc. Natl. Acad. Sci. USA 74, 5463–5467 (1977), or the Maxam-Gilbert method as described in Proc. Natl. Acad. Sci. USA 7.4, 560–564 (1977) may be employed.

It should, of course, be understood that not all expression vectors and DNA regulatory sequences will function equally well to express the DNA sequences of the present invention. Neither will all host cells function equally well with the same expression system. However, one of ordinary skill in the art may make a selection among expression vectors, DNA regulatory sequences, and host cells using the guidance provided herein without undue experimentation and without departing from the scope of the present invention.

The present invention further concerns a method for detecting a nucleic acid sequence coding for all or part of a mouse vav proto-oncogene protein or a related nucleic acid sequence comprising contacting the nucleic acid sequence with a detectable marker which binds specifically to at least a portion of the nucleic acid sequence, and detecting the marker so bound. The presence of bound marker indicates the presence of the nucleic acid sequence. Preferably, the nucleic acid sequence is a DNA sequence having all or part of the nucleotide sequence substantially as shown in FIG. 2 [SEQ. ID NO: 1]. Also preferred is a method in which the DNA sequence is a genomic DNA sequence. A DNA sample containing the DNA sequence may be isolated using various methods for DNA isolation which are well-known to those of ordinary skill in the art. For example, a genomic DNA sample may be isolated from tissue by rapidly freezing the tissue from which the DNA is to be isolated, crushing the tissue to produce readily digestible pieces, placing the crushed tissue in a solution of proteinase K and sodium dodecyl sulfate, and incubating the resulting solution until most of the cellular protein is degraded. The digest is then deprotenized by successive phenol/chloroform/ isoamyl alcohol extractions, recovered by ethanol precipitation, and dried and resuspended in buffer.

Also preferred is the method in which the nucleic acid sequence is an RNA sequence. Preferably, the RNA sequence is an mRNA sequence. Additionally preferred is the method in which the RNA sequence is located in the cells of a tissue sample. An RNA sample containing the RNA sequence may be isolated using various methods for RNA isolation which are well-known to those of ordinary skill in the art. For example, an RNA sample may be isolated from cultured cells by washing the cells free of media and then lysing the cells by placing them in a 4 M guanidinium solution. The viscosity of the resulting solution is reduced by drawing the lysate through a 20 gauge needle. The RNA is then pelleted through a $CsCl_2$ step gradient, and the supernatant fluid from the gradient carefully removed to allow complete separation of the RNA, found in the pellet, from contaminating DNA and protein.

The detectable marker useful for detecting a nucleic acid sequence coding for all or part of a mouse vav proto-oncogene protein or a related nucleic acid sequence, may be a labeled DNA sequence, including a labeled cDNA sequence, having a nucleotide sequence complementary to at least a portion of the DNA sequence coding for all or part of a mouse vav proto-oncogene protein.

The detectable marker may also be a labeled sense or antisense RNA sequence having a nucleotide sequence complementary to at least a portion of the DNA sequence coding for all or part of a mouse ray proto-oncogene protein The detectable markers of the present invention may be labeled with commonly employed radioactive labels, such as $^{32}P$ and $^{35}S$, although other labels such as biotin or mercury may be employed. Various methods well-known to those of ordinary skill in the art may be used to label the detectable markers. For example, DNA sequences and RNA sequences may be labeled with $^{32}P$ or $^{35}S$ using the random primer method.

Once a suitable detectable marker has been obtained, various methods well-known to those of ordinary skill in the art may be employed for contacting the detectable marker with the sample of interest. For example, DNA-DNA, RNA-RNA and DNA-RNA hybridizations may be performed using standard procedures known in the art. In a typical DNA-DNA hybridization procedure for detecting DNA sequences coding for all or part of a mouse ray proto-oncogene protein in genomic DNA, the genomic DNA is first isolated using known methods, and then digested with one or more restriction enzymes. The resulting DNA fragments are separated on agarose gels and denatured in situ. After prehybridization to reduce nonspecific hybridization, a radiolabeled nucleic acid probe is hybridized to the immobilized DNA fragments. The filter is then washed to remove unbound or weakly bound probe, and is then auto-radiographed to identify the DNA fragments that have hybridized with the probe.

The presence of bound detectable marker may be detected using various methods well-known to those of ordinary skill in the art. For example, if the detectable marker is radioactively labeled, autoradiography may be employed. Depending on the label employed, other detection methods such as spectrophotometry may also be used.

It should be understood that nucleic acid sequences related to nucleic acid sequences coding for all or part of squalene synthetase can also be detected using the methods described herein. For example, a DNA probe based on conserved regions of a mouse vav proto-oncogene protein (e.g., the helix-loop region, leucine zipper domain and cystein-rich [zinc-finger] domain) can be used to detect and isolate related DNA sequences (e.g., a DNA sequence coding for a rat vav proto-oncogene protein ). All such methods are included within the scope of the present invention.

As used in the present application and in this context, the term "related" means a nucleic acid sequence which is able to hybridize to an oligonucleotide probe based on the nucleotide sequence of a mouse ray proto-oncogene protein.

The present invention further concerns polypeptide molecules comprising all or part of a mouse vav proto-oncogene protein, said polypeptide molecules preferably having all or part of the amino acid sequence substantially as shown in FIG. 2 [SEQ. ID NO: 2].

The polypeptides of the present invention may be obtained by synthetic means, i.e., chemical synthesis of the polypeptide from its component amino acids, by methods known to those of ordinary skill in the art. For example, the solid phase procedure described by Houghton et al., Proc. Natl. Acad. Sci. 82, 5135 (1985) may be employed. It is preferred that the polypeptides be obtained by production in prokaryotic or eukaryotic host cells expressing a DNA sequence coding for all or part of a mouse vav proto-oncogene protein, or by in vitro translation of the mRNA encoded by a DNA sequence coding for all or part of a mouse vav proto-oncogene protein. For example, the DNA sequence of FIG. 2 [SEQ. ID NO: 1] may be synthesized using PCR as described above and inserted into a suitable expression vector, which in turn may be used to transform a suitable host cell. The recombinant host cell may then be cultured to produce a mouse vav proto-oncogene protein. Techniques for the production of polypeptides by these means are known in the art, and are described herein.

The polypeptides produced in this manner may then be isolated and purified to some degree using various protein purification techniques. For example, chromatographic procedures such as ion exchange chromatography, gel filtration chromatography and immunoaffinity chromatography may be employed.

The polypeptides of the present invention may be used in a wide variety of ways. For example, the polypeptides may be used to prepare in a known manner polyclonal or monoclonal antibodies capable of binding the polypeptides. These antibodies may in turn be used for the detection of the polypeptides of the present invention in a sample, for example, a cell sample, using immunoassay techniques, for example, radioimmunoassay or enzyme immunoassay. The antibodies may also be used in affinity chromatography for purifying the polypeptides of the present invention and isolating them from various sources.

The polypeptides of the present invention have been defined by means of determined DNA and deduced amino acid sequencing. Due to the degeneracy of the genetic code, other DNA sequences which encode the same amino acid sequence as depicted in FIG. 2 [SEQ. ID NO: 2] may be used for the production of the polypeptides of the present invention. In addition, it will be understood that allelic variations of these DNA and amino acid sequences naturally exist, or may be intentionally introduced using methods known in the art. These variations may be demonstrated by one or more amino acid differences in the overall sequence, or by deletions, substitutions, insertions, inversions or additions of one or more amino acids in said sequence. Such amino acid substitutions may be made, for example, on the basis of similarity in polarity, charge, solubility, hydrophobicity, hydrophilicity and/or the amphiphathic nature of the residues involved. For example, negatively charged amino acids include aspartic acid and glutamic acid; positively charged amino acids include lysine and arginine; amino acids with uncharged polar head groups or nonpolar head groups having similar hydrophilicity values include the following: leucine, isoleucine, valine; glycine, alanine; asparagine, glutamine; serine, threonine; phenylalanine, tyrosine. Other contemplated variations include salts and esters of the aforementioned polypeptides, as well as precursors of the aforementioned polypeptides, for example, precursors having N-terminal substituents such as methionine, N-formylmethionine and leader sequences. All such variations are included within the scope of the present invention.

The following examples are further illustrative of the present invention. These examples are not intended to limit the scope of the present invention, and provide further understanding of the invention.

EXAMPLE I

ISOLATION AND CHARACTERIZATION OF MOUSE VAV PROTO-ONCOGENE

A. MATERIALS AND METHODS

1. Gene Transfer Assay

NIH3T3 mouse cells were transfected with various amount (1 ng to 1 μg) of linearized plasmid DNA in the presence of 20 μg of carrier (calf thymus) DNA as described in Graham, F. L. and van der Eb, A. J., Virology 52, 456–467 (1975). Foci of transformed cells were scored after 14 days. To isolate G418-resistant colonies, NIH3T3 cells were co-transfected with 20 ng of pSVneo DNA and 1 μg of the desired plasmid DNA as described in Fasano, O. et al., Mol. Cell Biol. 4, 1695–1705 (1984).

2. Mouse vav cDNA clones cDNA libraries derived from WEH1-3 and EL-4 hematopoietic cell lines (Stratagene, La Jolla, Calif.) were screened under partially relaxed hybridization conditions (42° C. in 5 X SSC. [SSC.=35.06 g/1 NaCl, 17.65 g/1 Na-citrate, pH 7.0], 40% formamide, 1 X Denhardt's solution) using as a probe a [$^{32}$P]-labeled insert of pSK8 (ATCC. 41060), a plasmid containing a partial cDNA clone of the human vav proto-oncogene [Katzav, S. et al., supra]. Recombinant phages carrying the longest inserts (2.8 kbp) were subcloned in Bluescript KS (Stratagene) to generate pMB24 and pMB25. These mouse vav cDNA clones were submitted to nucleotide sequence analysis by the dideoxy chain termination method [Sanger, F. et al., Proc. Natl. Acad. Sci. USA 74, 5463–5467 (1977)] using double-stranded DNA, synthetic oligonucleotides as primers and modified T7 DNA polymerase (Sequenase, United States Biochemicals, Cleveland, Ohio).

3. Expression plasmids

Mouse vav expression plasmids. pJC11 was generated by subcloning the entire 2.8 kbp cDNA insert of pMB24 into the EcoRI site of pMEX, a mammalian expression vector carrying a multiple cloning site flanked by an MSV LTR (Maloney sarcoma virus, long terminal repeat) and a SV40 polyadenylation signal [Martin-Zanca, D. et al., Mol. Cell Biol. 9, 24–33 (1989)]. Subcloning procedures involved digestion of pMB24 DNA with the restriction endonuclease Eco RI, purification of the 2.8 kbp cDNA insert and religation to Eco RI-digested pMEX DNA. These procedures are standard recombinant DNA techniques and are described in detail in Maniatis, T. et al., *Molecular Cloning: A Laboratory Manual*, Cold Spring Harbor Laboratory, Cold Spring Harbor, N.Y. (1982). The 2.8 kbp EcoRI DNA insert of pMB24 was isolated after partial digestion to avoid cleavage at the internal EcoRI site (nucleotides 2251–2256, FIG. 2) [see SEQ. ID NO: 1]. pJC12 was obtained by deleting an internal 280 bp DNA fragment encompassed between the Sal I cleavage site present in the MCS and the unique Nru I site located at position 184–189 (FIG. 2) [see SEQ. ID NO: 1]. This Nru I site lies just upstream of a second ATG codon (nucleotides 209–211, FIG. 2) [see SEQ. ID NO: 1] that serves as a translational initiator in this plasmid. pJC17 was generated by replacing the internal 607 bp Kpn I-Stu I DNA fragment (nucleotides 992–1599 in FIG. 2) [see SEQ. ID NO: 1] of pJC12 by a mutant DNA fragment carrying a single point mutation (T→A) at position 1595 (FIG. 2) [SEQ. ID NO: 1]. The mutated fragment was obtained by PCR-aided amplification of the 607 bp Kpn I-Sru I DNA fragment using a mismatched 3' amplimer. pJC18 was generated by replacing the internal 186 bp ECO RV-Bam HI DNA fragment (nucleotide 1638-1824 in FIG. 2) [see SEQ. ID NO: 1] of pJC12 with a mutant DNA fragment carrying a single point mutation (G→C) at position 1738 (FIG. 2) [see SEQ. ID NO: 1]. The mutated fragment was obtained by PCR-aided amplification of the 186 bp Eco RV-Bam HI DNA fragment using a mismatched 5' amplimer. pJC19 was generated by replacing the internal 72 bp Eco RV-Nco I DNA fragment (nucleotides 1638–1800 in FIG. 2) [see SEQ. ID NO: 1] of pJC12 by a mutant DNA fragment carrying a single point mutation (C→G) at position 1670 (FIG. 2) [see SEQ. ID NO: 1]. The mutated DNA fragment was obtained by chemical synthesis.

Human vav gene expression plasmids. pJC7 was obtained by inserting the 2.9 kbp EcoRI cDNA clone of pSK65 [Katzav, S. et al., supra] into the unique EcoRI site of pMEX. pJC13 was obtained by replacing the internal 850 bp Pst I DNA fragment of pJC7 by a similar DNA fragment generated by PCR-aided amplification using a 5' amplimer having SEQ. ID. NO.: 3 (5'CCGGCTGCAGGCCACCATG-GAGCTGTGGCGCCAATGCACC3'[see SEQ ID No.: 3].) that carried an insertion of four nucleotides (underlined). The inserted bases reconstitute the coding sequences presumably missing in pJC7. pJC15 was obtained by replacing the internal 552 bp Bal I fragment of pJC7 by a similar PCR-generated DNA fragment carrying a single point mutation (T→C) in the triplet coding for the first cysteine residue of the first zinc-finger like structure (Table 2). To obtained the mutated 552 bp Bal I fragment, an 87 bp Bal I-Stu I fragment was amplified by PCR using a 3' amplimer that carried the mismatch needed to introduce the required T→C. mutation. This PCR-generated BalI-StuI fragment was then ligated to the wild type 465 bp Stu I-Bal I DNA fragment obtained from pJC7. The nucleotide sequence of each of the above expression plasmids was verified by direct sequencing of double stranded DNA. Moreover, these expression plasmids directed the synthesis of the expected vav protein as determined by immunoprecipitation analysis of G418-resistant NIH3T3 cells generated by co-transfection of these plasmids with the selectable marker pSV2neo.

4. Southern and Northern blot analysis

High molecular weight DNA was digested to completion with appropriate restriction endonucleases, electrophoresed in 0.7% agarose gels and submitted to Southern transfer analysis as described in Southern, E. M., J. Mol. Biol. 98, 503–517 (1975). Total cellular RNA was extracted by the guanidium thiocyanate method [Chirgwin, J. M. et al., Biochemistry 18, 5294–5299 (1979)] and purified by centrifugation through cesium chloride. Poly(A)-containing RNA was isolated by retention on oligo(dT) columns (Collaborative Research, Bedford, MA). Total RNA (10 µg) or poly(A)-selected RIgA (3 µg) were submitted to Northern transfer analysis as described in Lehrach, H. et al., Biochemistry 16, 4743–4751 (1977). The nitrocellulose filters were hybridized with various $^{32}$P-labeled nick translated probes for 48 hours under stringent conditions (42° C. in 5 X SSC, 50% formamide, 1 X Denhardt's solution).

5. Protein analysis

Figure 1:
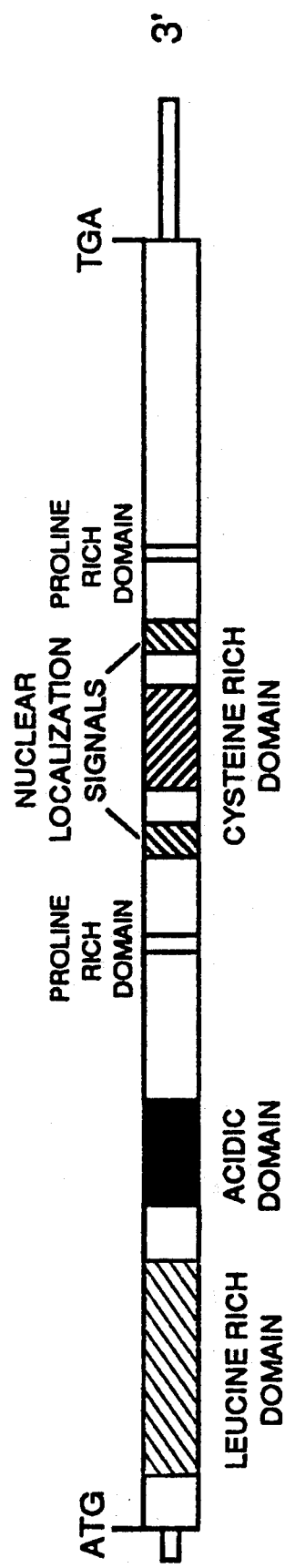
FIG. 1 shows a schematic diagram of a nucleotide sequence analysis of a mouse vav proto-oncogene cDNA clone. Untranslated 5' and 3' sequences are represented by a thin bar. Coding sequences are depicted by a thicker box and are flanked by the initiator (ATG) and terminator (TGA) codons. Highlighted domains include the leucine-rich domain (shaded box); the acidic region (black box) two proline-rich stretches (open box); two putative nuclear localization signals (left hatched box) and a cystein-rich region (right hatched box).

Transfection of NIH3T3 cells, isolation of transformed cells, selection of G418-resistant colonies, metabolic labeling of cells with [$^{35}$S-]methionine, immunoprecipitation with various antisera and SDS-PAGE analysis were carried out as described in Martin-Zanca, D. et al., Mol. Cell Biol. 9, 24–33 (1989). The rabbit antiserum used to immunoprecipitate the vav proteins was raised against a synthetic 14-mer peptide having SEQ. ID. NO.: 6 (KDKLHRRAQDKKRN) whose sequence corresponds to either amino acid residues 576 to 589 of a mouse vav protein (FIG. 1) or to residues 528 to 541 of the human vav oncogene product [Katzav, S. et al., supra].

B. RESULTS

1. Nucleotide Sequence of the Mouse Vav Proto-oncogene

Independent mouse cDNA libraries derived from two hematopoietic cell lines (WEHI-3 and EL-4) were used to isolate cDNA clones of the mouse vav proto-oncogene. WEHI-3 (ATTC. TIB 68) is a myeloid cell line and EL-4 (ATCC. TIB 39) cells were established from a mouse T-cell lymphoma. A total of 12 cDNA clones were isolated. Those recombinant phages containing the longest inserts from each library (2792 Kbp from the WEHI-3 and 2788 Kbp from the EL-4 cDNA library) were excised by using a helper phage, circularized and propagated in E. coli DH5 cells as plasmids. These plasmids, designated pMB24 (WEHI-3 library) and pMB25 (EL-4 library) were subsequently submitted to nucleotide sequence analysis using standard dideoxy sequencing techniques as described in Sanger et al., supra.

FIG. 2 [SEQ. ID NO: 1] depicts the nucleotide sequence of the 2,793 bp long insert of pMB24. pMB25, the cDNA clone derived from EL-4 T-cell cDNA library possessed an identical sequence extending from nucleotide 5 to 2792. These results indicate that these cDNA clones are faithful representatives of normal vav transcripts in mouse hematopoietic cells. Analysis of the nucleotide sequence of pMB24 revealed a long open reading frame extending from nucleotides 14 to 2597. The first in-frame ATG codon (nucleotides 14–16) is part of the canonical GCCACCATGG motif SEQ. ID. NO.: 7 characteristic of efficient mammalian translational initiators [Kozak, M., Nucleic Acids Res. 15, 8125–8148, (1987)]. Analysis of mouse vav cDNA clones carrying additional 5' sequences revealed an inframe terminator codon (TGA) 45 nucleotides upstream of the beginning of the pMB24 clone (FIG. 2) [see SEQ. ID NO: 1]. Therefore, it is likely that vav protein synthesis initiates at this ATG codon. If so, a mouse vav proto-oncogene would code for an 844 amino acid-long polypeptide with a predicted molecular mass of 97,303 daltons. This open reading frame is followed by a stretch of 195 bp of 3' non-coding sequences which includes a translational terminator TGA (nucleotides 2598–2600) and the consensus polyadenylation signal AATAAA (positions 2774 to 2779) (FIG. 2) [see SEQ. ID NO: 1]. Analysis of additional mouse vav cDNA clones carrying additional 3' sequences revealed the presence of a polyA tail just two nucleotides downstream from the end of clone pMB24.

The predicted amino acid sequence of the putative 844 amino acid-long mouse vav protein revealed a leucine-rich domain extending from amino acid residues 33 to 102 (FIG. 2) [see SEQ. ID NO: 2]. This domain includes a short sequence, Ala-Leu-Arg-Asp-X-Val which is also present in each of the three members of the myc oncogene family. This conserved motif is located within an amphipathic helix-loop-helix domain, which in myc proteins is required for dimerization and DNA binding [Murre, C. et al., Cell 56, 777–783 (1989)]. This sequence, however, is not shared by other DNA binding proteins such as Myo D1, daughterless and one of the members of the achaete-scute complex that exhibit similar helix-loop-helix motifs [Murre, C. et al., Cell 58, 537–544 (1989)]. The amino terminal leucine-rich domain of the vav proto-oncogene has additional structural homologies with the members of the myc gene family. They include a heptad repeat of hydrophobic residues, of which three (four in the myc proteins) are leucines. This leucine zipper-like domain is separated from the shared Ala-Leu-Arg-Asp-X-Val sequence by a putative hinge region that contains two proline residues. A similar combination of helix-loop-helix structure followed by a heptad repeat of hydrophobic sequences has been shown to be involved in ligand binding and dimerization of nuclear receptors [Fawell, S. E. et al., Cell 60, 953–962 (1990)].

Other relevant features identified in the deduced amino acid sequence of a mouse vav proto-oncogene product include: (i) a highly acidic 45 amino acid-long domain (residues 132–176) in which 22 residues (49%) are either glutamine or aspartic acid; (ii) two stretches of proline residues (positions 336 to 340 and 606 to 609) that may represent hinge regions; (iii) a putative protein kinase A phosphorylation site (residues 435 to 440); (iv) two putative nuclear localization signals (residues 486 to 493 and 575 to 582); (v) a cysteine-rich sequence which includes two metal binding motifs Cys-$X_2$-Cys-$X_{13}$-Cys-$X_2$-Cys (residues 528 to 548; SEQ. ID. NO.: 4) and His-$X_2$-Cys-$X_6$-Cys-$X_2$-His (residues 553 to 566;

SEQ. ID. NO.: 5). The former is similar to zinc finger motif found in transcriptional activators such as the adenovirus E1A, yeast GAL4 and certain steroid receptors [Johnson et al., Annu. Rev. Biochem. 58 799–839 (1989)]. The overall alignment of cysteine residues in this domain (Cys-X$_2$-Cys-X$_{13}$-Cys-X$_2$-Cys-X$_7$-Cys-X$_6$-Cys) (SEQ. ID. NO.: 8) is also reminiscent of the tandem motifs found in the amino terminal domain of the various members of the protein kinase C family and in a diacyglycerol kinase [Coussens et al., Science 233 859–866 (1986) and Sakane, F. et al., Nature 344 345–348 (1990)].

2. Homology with the Human Vav Oncogene

Alignment of the deduced amino acid sequences of a mouse and human ray gene products reveal a remarkable degree of homology. The predicted mouse vav proto-oncogene sequence (amino acid residues 3 to 844) is 91.2% identical (769 residues) to that of its human counterpart. Of the 73 different residues, at least 30 are conservative substitutions, thus yieldig an overall homology of 94.8% between human and murine vav proteins. More importantly, all of the other relevant domains previously identified in the product of the human vav gene, including the acidic domain, the two proline hinge regions, the putative protein kinase A phosphorylation site, the cystein-rich sequence that can fold into zinc finger-like structures and the putative nuclear localization signals, are also present in a mouse vav gene product (FIG. 2) [see SEQ. ID NO: 1]. The mouse vav protein is one amino acid shorter (844 residues) due to the presence of a single Ile$^{717}$ residue instead of the sequence Thr$^{717}$ Val$^{718}$ found in its human counterpart.

Comparison of a mouse ray proto-oncogene product with that of the human vav oncogene suggest that its 67 amino terminal amino acids were replaced by 19 unrelated residues derived from the bacterial Tn5 gene. Therefore, the human vav oncogene retains the carboxy-terminal moiety of the leucine-rich domain which includes the leucine repeat, but not the Ala-Leu-Arg-Asp-X-Val (SEQ ID NO: 9) sequences shared with each of the members of the myc gene family.

3. Expression of the Mouse Vav Proto-Oncogene

It has been previously shown that the human vav proto-oncogene is specifically expressed in cells of hematopoietic origin regardless of their differentiation lineage [Katzav, S. et al., supra] confirms this pattern of expression. As summarized in Table 1, vav gene transcripts were identified in hematopoietic cells of myeloid (macrophage-derived 7.1.3 cell line), lymphoid (MOPC 315 plasmacytoma and A20 B-lymphocyte cell lines) and erythroid (Friend erythroleukemia cells, F412B2 clone) origin. The levels of vav gene expression in undifferentiated mouse F412B2 cells were comparable to those present in the differentiated erythroid-like cells obtained by treatment of F412B2 cells with DMSO or HMBA. Similar results were obtained when human HEL and HL60 cells were induced to differentiate along different hematopoietic lineages [Katzav, S. et al., supra].

Northern blot analysis of RNA isolated from mouse fibroblastic cell lines failed to reveal detectable levels of vav gene expression (Table 1). These results were independent of the proliferative state of the cells since neither quiescent or serum-stimulated BALB3T3 cells possessed detectable vav gene transcripts. Similarly, vav gene expression was not found to correlate with the tumorigenic state of the cell since neither non-tumorigenic NIH3T3 cells or tumorigenic NIH3T3-derived Ψ2 cells expressed detectable vav gene sequences (Table 1).

Figure 3:
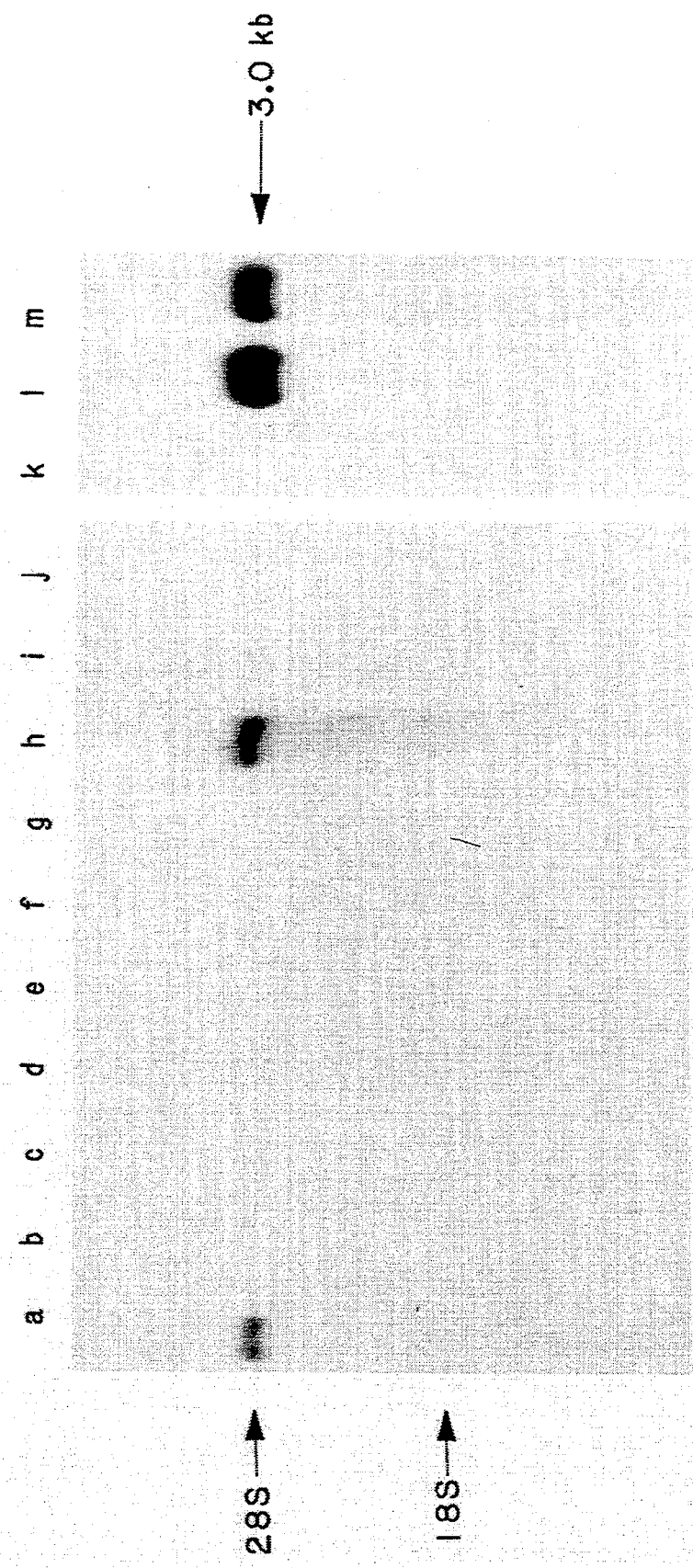
FIG. 3 shows detection of mouse vav gene transcripts. Two micrograms of poly A-selected RNA isolated from adult mouse tissue including (a) lung; (b) heart; (c) testes; (d) muscle; (e) intestine; (f) brain; (g) kidney; (h) spleen; (i) ovaries; (j) liver; and from murine cell lines including (k) NIH3T3 fibroblasts; (1) A20 B-lymphocyte and (m) MOPC 315 plasmacytoma cells were submitted to Northern transfer analysis. Nitrocellulose filters were hybridized under stringent conditions (50% v/v formamide, 42° C.) to $5 \times 10^7$ cpm of a [$^{32}$P]-labeled nick-translated DNA fragment corresponding to the entire insert of pMB24. The hybridized filter was exposed to Kodak X-OMAT film for 24 hours at −70° C. with the help of intensifier screens. S. cerevisiae 23S and 18S ribosomal RNAs were used as size markers. The migration of the 3 kb mouse vav proto-oncogene transcript is indicated by a thick arrow.

To determine the pattern of expression of the vav proto-oncogene in vivo, RNAs were isolated from various mouse tissues and submitted to Northern blot analysis. vav gene transcripts were observed in spleen and lung tissues but not in brain, heart, intestine, muscle, ovaries or testes (FIG. 3). Expression of the vav gene in spleen cells indicates that this locus is expressed in hematopoetic cells in vivo. The presence of vav gene transcripts in lung raises the possibility that this gene may also be expressed in non-hematopietic cell types. However, lungs are known to contain high levels of infiltrating macrophages that may account for the results depicted in FIG. 3.

4. Identification of the Mouse Ray Proto-Oncogene Product

To identify the product of a mouse vav proto-oncogene, rabbits were immunized with a peptide whose sequence corresponded to that of an amphilic region conserved in a mouse and human vav gene proteins (amino acid residues 576 to 589 of FIG. 2) [see SEQ. ID NO: 2]. Immunoprecipitation of [$^{35}$S-methionine]-labeled extracts of PAb280, a mouse B-cell hybridoma and PMMI, a mouse T-cell hybridoma with this anti-vav peptide antiserum revealed various polypeptides ranging in size between 75,000 and 105,000 daltons. The most intense band corresponded to a protein of about 95,000 daltons, a size that corresponds well with that expected for the vav gene product.

To establish whether this 95,000 dalton polypeptide was indeed the product of a mouse vav gene, an expression plasmid was generated by subcloning the entire cDNA insert of pMB24 into pMEX, an eukaryotic expression vector [Martin-Zanca, D. et al., Mol. Cell Biol. 9, 24–33 (1989)]. The resulting plasmid, designated pJC11, was co-transfected into NIH3T3 cells with pSVneo and colonies of G418-resistant cells were selected for immunoprecipitation analysis. As illustrated in FIGS. 4C and D, cells transfected with pJC11 DNA expressed a 95,000 dalton protein indistinguishable from that present in mouse pAB280 and PMMI hybridoma cell lines. Moreover, immunoprecipitation of this 95,000 dalton protein was specifically blocked by preincubation with the immunizing peptide (FIG. 4D). These results indicate that p95vav is the product of a mouse vav proto-oncogene.

Immunoprecipitation analysis of either hematopoietic cells or vav-transfected NIH3T3 clones consistently revealed a mior protein species that migrates as a diffuse band of about 105,000 daltons. Immunoprecipitation of this protein could be specifically blocked by competition with the immunizing peptide. Whether this protein represents a modified form of p95$^{vav}$ or a different protein able to complex with the vav gene product awaits further biochemical characterization.

5. Malignant Activation of the Vav Proto-Oncogene

Figure 5:
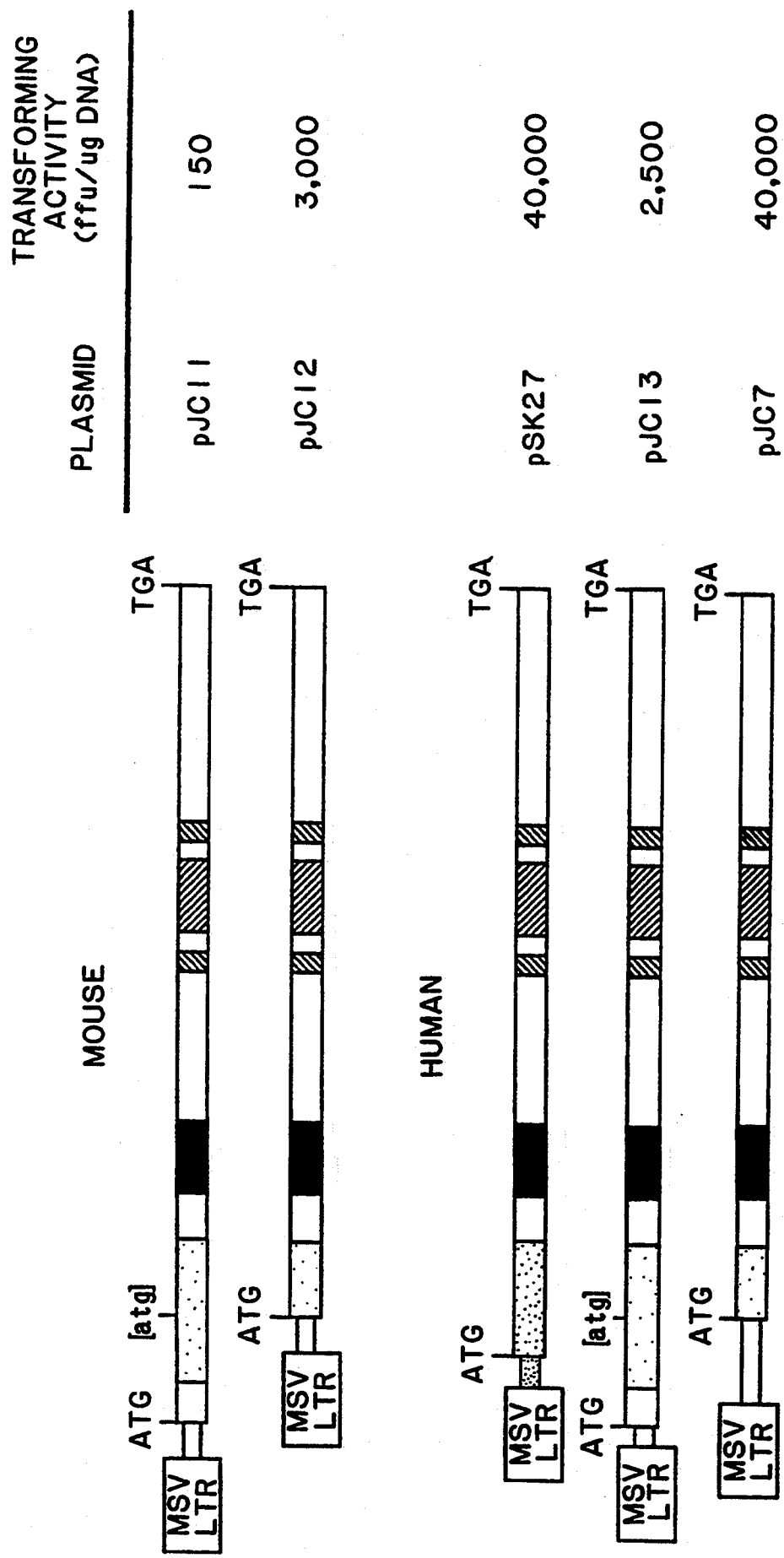
FIG. 5 shows the mechanism of activation of mouse and human ray oncogenes. Schematic representation of pMEX-derived expression vectors carrying normal and mutated vav cDNA clones. Symbols are those shown in FIG. 1A. The presence of an MSV-LTR in each of these plasmids is also indicated. Bacterial Tn5-derived sequences present in the pSK27 plasmid containing a human vav oncogene [Katzav, S. et al., supra] are indicated by a dashed box. The [atg] symbol represent an in-frame translational initiator used by pJC12 and pJC7. This triplet codes for the methionine residues underlined in FIG. 2. The right column indicates the relative transforming activity of these plasmids (expressed as focus forming units per microgram of linearized plasmid DNA) when tested in gene transfer assays using NIH3T3 cells as recipients.

Transfection of NIH3T3 cells with pJC11 DNA, an expression plasmid carrying a mouse vav proto-oncogene, did not revealed significant levels of morphologic transformation (FIG. 5). These results suggest that the transforming properties of the vav oncogene might be due to the absence of the myc-related amino-terminal domain and/or to the presence of the bacterial Tn5- derived sequences. To resolve this question, a truncated mouse vav gene was generated by deleting those nucleotide sequences of pJC11 DNA encompassed between the 5' Sal I site of the pMEX multiple cloning site and a NruI site that lies just upstream of the second in-frame ATG codon (nucleotides 301 to 303 in FIG. 2) [see SEQ. ID NO: 1]. The resulting plasmid, designated pJC12, codes for a truncated mouse vav protein that lacks 65 of the 67 amino-terminal residues absent in the human vav oncogene product (Katzav, S. et al., supra). Transfection of NIH3T3 cells with pJC12 DNA resulted in the appearance of about 3,000 foci of transformed cells per microgram of transfected DNA (FIG. 5). Immunoprecipitation of [$^{35}$S-methionine]-labeled extracts of NIH3T3 cells transformed by pJC12 DNA with anti-vav peptide antibodies revealed expression of the expected 88,000 dalton protein (not shown). These results indicate that truncation of the amino-terminal domain of a mouse vav proto-oncogene product can activate its transforming potential.

The transforming activity of pJC12 DNA is at least one order of magnitude lower than that of pSK27 DNA, the expression plasmid containing the human vav oncogene (FIG. 5). To examine whether the Tn5-derived sequences also contribute to the transforming activity of the human vav oncogene, we generated pJC7, a pMEX-derived expression plasmid similar to pJC11 except that the vav sequences were of human origin. Since the longest human vav proto-oncogene cDNA clone ends four nucleotides short of the physiological ATG initiator codon, translation from pJC7 DNA is likely to start in the second in-frame ATG, the initiator codon used by pJC12. Transfection of NIH3T3 cells with pJC25 DNA resulted in the appearance of about 40,000 foci of transformed cells per microgram of transfected DNA, a transforming activity comparable to that of the human vav oncogene (FIG. 5). These results indicate that the Tn5-derived sequences present in the human vav oncogene do not contribute to its transforming activity. Moreover, they demonstrate that truncation of the amino terminal domain of the vav gene product is sufficient to activate its neoplastic properties.

Figure 6:
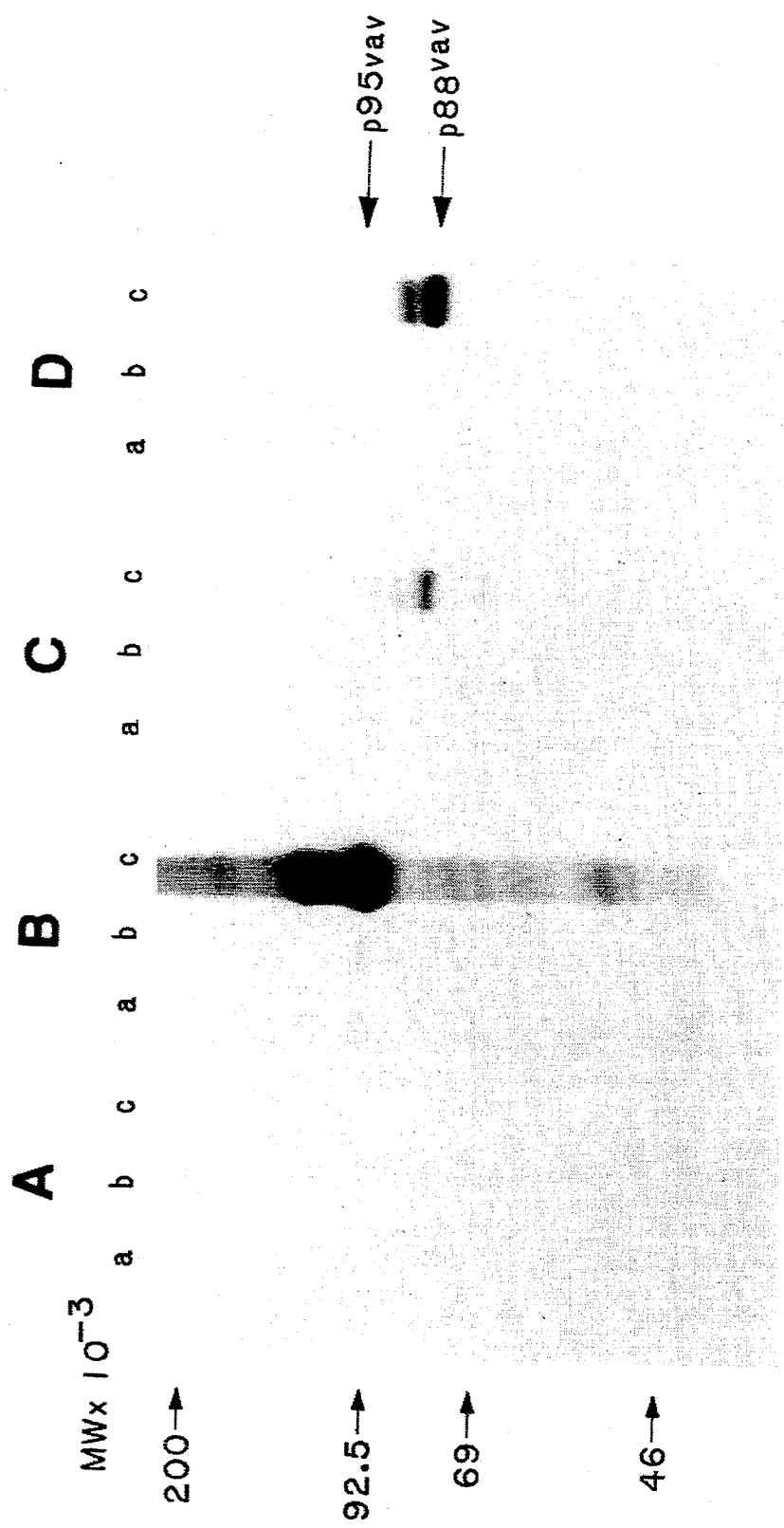
FIG. 6 shows that overexpression of wild type p95$^{vav}$ protein can induce morphologic transformation of NIH3T3 cells. [$^{35}$S methionine]-labeled cell extracts of (A) NIH3T3 cells; (B) NIH3T3 cells transformed by pJC13, an expression plasmid containing a full vav cDNA clone; (C) NIH3T3 cells transformed by pJC7, an expression plasmid containing a vav cDNA clone coding for a protein lacking the amino terminal domain (amino acid residues 1 to 65); and (D) NIH3T3 cells transformed by pSK27, an expression plasmid containing the human vav oncogene were immunoprecipitated with (a) normal rabbit serum and (b,c) a rabbit antiserum raised against a ray peptide either (b) in the presence or (c) in the absence of 10 μg of competing peptide. Immunoprecipitates were analyzed as indicated in the legend to FIG. 4. The migration of the wild type p95$^{vav}$ and the truncated p88$^{vav}$ proteins is indicated by thick arrows. Co-electrophoresed molecular weight markers are those described in FIG. 4 and ovalbumin (46,000).

Finally, it was determined whether the human vav proto-oncogene possesses transforming activity. For this purpose, pJC7 was modified by adding the four nucleotides (ATGG) presumably missing in our human vav proto-oncogene cDNA clone. The resulting plasmid, pJC13, can only transform NIH3T3 cells with about 5% the activity of its parental clone, pJC7 (FIG. 5). Analysis of NIH3T3 cells transformed by pJC13 DNA consistently exhibited levels of expression of the normal p95$^{vav}$ proto-oncogene product 5- to 10-fold higher than those of the truncated vav protein found in cells transformed by pJC7 or pSK27 (FIG. 6). These results indicate that the human vav proto-oncogene can only induce malignant transformation if overexpressed in NIH3T3 cells.

6. Identification of a Second Human Vav Oncogene: Mechanism of Activation

Figure 7:
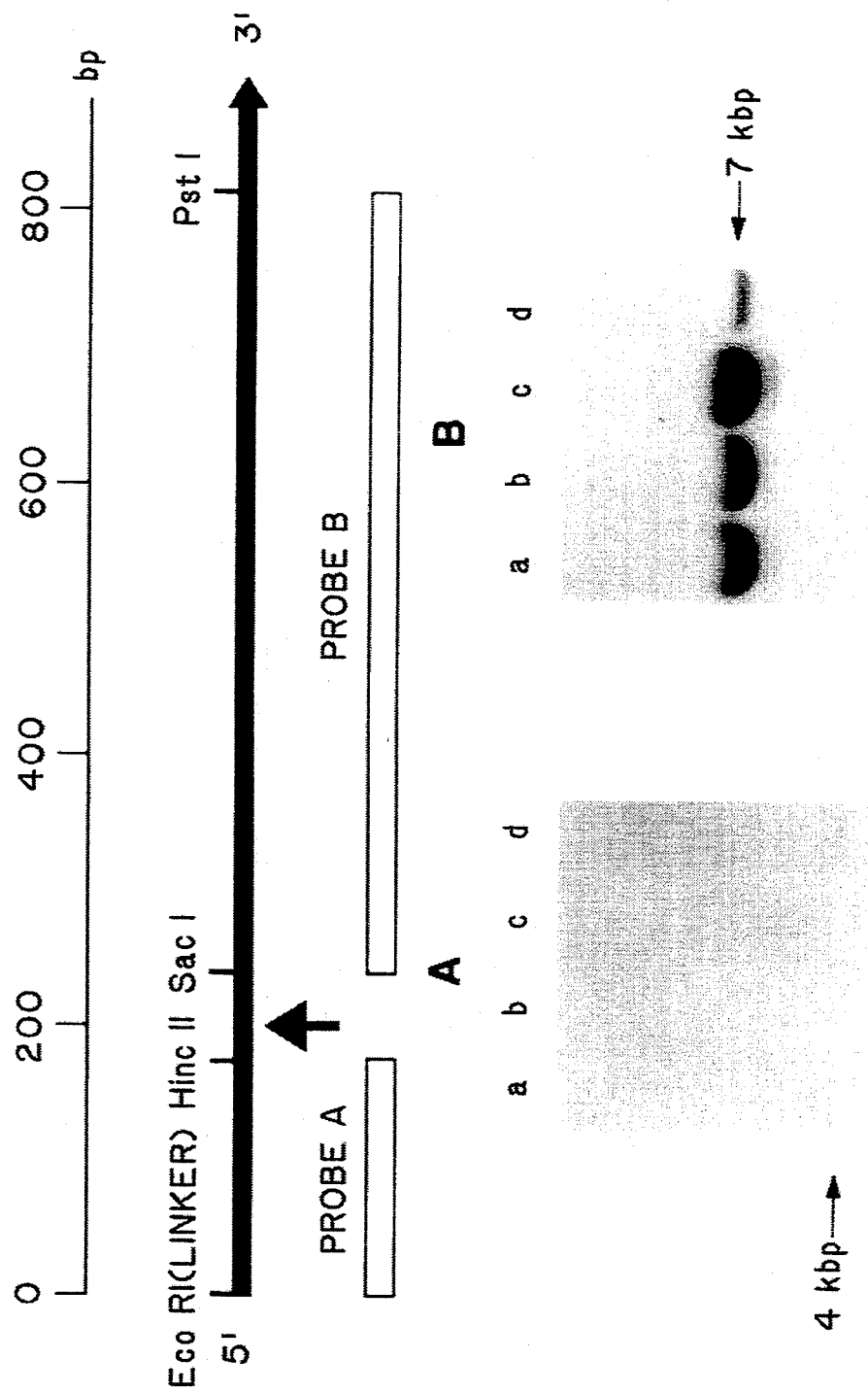
FIG. 7 shows the identification and mechanism of activation of a second human vav oncogene. DNAs (10 μg) isolated from (a) a nude mouse tumor induced by NIH3T3 cells that contain a human vav oncogene (Katzav, S. et al., supra); (b,c) nude mouse tumors induced by (b) second cycle- and (c) third cycle-transformants derived from transfection of NIH3T3 cells with human breast carcinoma DNA and (d) T24 human cells, were digested with Sac I and submitted to Southern transfer analysis. Hybridization was conducted for 48 hours under stringent conditions (50% v/v formamide, 42° C.) using 5 × 10$^7$ cpm of [$^{32}$P]-labeled nick-translated probes corresponding to (A) a 180 bp EcoRI-Hinc II and (B) a 575 bp Sac I-Pst I DNA fragment of pSK65, a Bluescript-derived plasmid containing a human vav proto-oncogene cDNA clone [Katzav, S. et al., supra.]. Filters were exposed to Kodak X-OMAT film at −70° C. for (A) 10 days or (B) 3 days in the presence of intensifier screens. Co-electrophoresed λ Hind III DNA fragments were used as size markers. The migration of the genomic (A) 4 kbp and (B) 7 kbp Sac I DNA fragments is indicated by arrows. The precise location of the pSK65-derived probes is indicated in the upper diagram. The vertical arrow indicates the break-point caused by the genomic rearrangement that activated the previously characterized human vav oncogene [Katzav, S. et al., supra].

A second human vav oncogene has been identified during the course of gene transfer experiments using DNAs isolated from mammary carcinomas (unpublished observations). To investigate whether this independently isolated vav oncogene also became activated by truncation of its amino terminus, two DNA probes were prepared by PCR-aided amplification of defined domains of the 5' region of pSK65, a human vav proto-oncogene cDNA clone (Katzav, S. et al., supra). The first probe is a 180 bp Eco RI-Hinc II DNA fragment which contains the 5' end of the human vav proto-oncogene cDNA clone, a region known to be absent in its transforming allele (FIG. 7A). The second probe is a 575 bp Sac I-Pst I DNA fragment that corresponds to a region located 3' to the leucine-rich domain and encompasses those sequences coding for the acidic region of the vav protein. As shown in FIG. 7B, the 575 bp Sac I-Pst I probe recognized an internal 7 kbp Sac I fragment of normal human DNA which was also present in NIH3T3 cells transformed by the two independently isolated human vav oncogenes. In contrast, the most 5' 180 bp Eco RI-Hinc II probe only hybridized to normal human DNA (FIG. 7A). These results indicate that a second human vav oncogene identified during gene transfer of mammary carcinoma DNA into NIH3T3 cells, has also lost those 5'sequences coding for the amino-terminal moiety of the vav leucine-rich region.

7. Contribution of the Cysteine-Rich Domains to the Biological Activity of the Vav Gene Products The mouse and human vav gene products contain two structures that resemble metal binding domains. The first structure, located in residues 528–548 of a mouse p95$^{vav}$ protein (FIG. 2), has a Cys-X$_2$-Cys-X$_{13}$-Cys-X$_2$-Cys sequence pattern (SEQ. ID. NO.: 4) This motif has been previously found in several transcriptional activators such as the products of the adenovirus E1a, the yeast GAL 4 and various steroid receptor genes [Johnson, P. F. et al., Annu. Rev. Biochem. 58, 799–839 (1989)]. The second structure possesses a sequence pattern (His-X$_2$-Cys-X$_6$-Cys-X$_2$-His, SEQ. ID. NO.: 5) that has not be previously described. The spacing of the cysteine residues along these putative metal binding structure (Cys-X$_2$-Cys-X$_{13}$-Cys-X$_2$-Cys-X$_7$-Cys-X$_6$-Cys, SEQ. ID. NO.: 8), is also reminiscent of the phorbol ester binding domain of protein kinase C [Ono, Y. et al., Proc. Natl. Acad. Sci. USA 86, 4868–4871 (1989)].

To test whether these structures are required for ray gene function, single point mutations were engineered in pJC12 and pJC7 DNAs that eliminated some of the conserved cystein and histidine-coding triplets. pJC12 and pJC7, two expression plasmids capable of inducing the malignant transformation of NIH3T3 cells, provide a reliable biological assay to measure vav gene activity. In order to verify the presence of the desired mutation, each of the mutated plasmids was submitted to nucleotide sequence analysis. In addition, these plasmids were transfected into NIH3T3 cells to verify that they directed the synthesis of the expected vav gene products (not shown).

As summarized in Table 2, replacement of the first or third cysteines of the metal binding-like domain by serine residues completely abolished the transforming activity of a mouse ray gene present in pJC12. Similar results were obtained when the first cysteine of the human ray gene was replaced by an arginine residue (Table 2). Finally, substitution of the histidine residue corresponding to the first position of a mouse His-X$_2$-Cys-X$_6$-Cys-X$_2$-His motif (SEQ. ID. NO.:5), also abolished vav transforming activity (Table 2). This histidine residue is one of five vav amino acids shared by the phorbol ester domains of protein kinase C. These results indicate that the overall structure of the cysteine-rich domain of vav gene proteins is required for their biological function.

All publications and patents referred to in the present application are incorporated herein by reference to the same extent as if each individual publication or patent was specifically and individually indicated to be incorporated by reference.

TABLE 1

Expression of a mouse vav proto-oncogene in cells of murine origin[a]

| CELL LINE | CELL TYPE | vav GENE EXPRESSION | REFERENCE |
|---|---|---|---|
| 7.1.3 | Macrophage | + | Baumbach et al., 1987[b] |
| MOPC 315 | Plasmacytoma | + | ATCC TIB 23 |
| A 20 | B lymphocyte | + | ATCC TIB 208 |
| F412B2 | Erythroleukemia (undifferentiated) | + | Coppola and Cole, 1986[c] |
| F412B2 + HMBA | Erythroleukemia (differentiated) | + | |
| NIH3T3 | Fibroblast (non-tumorigenic) | − | Jainchill et al., 1969[d] |
| NIH3T3/ψ-2 | Fibroblast (tumorigenic) | − | Mann et al., 1983[e] |
| A31 | Fibroblast (quiescent) | − | ATCC CCL 163 |
| A31 + serum | Fibroblast (proliferating) | − | |

Figure 4:
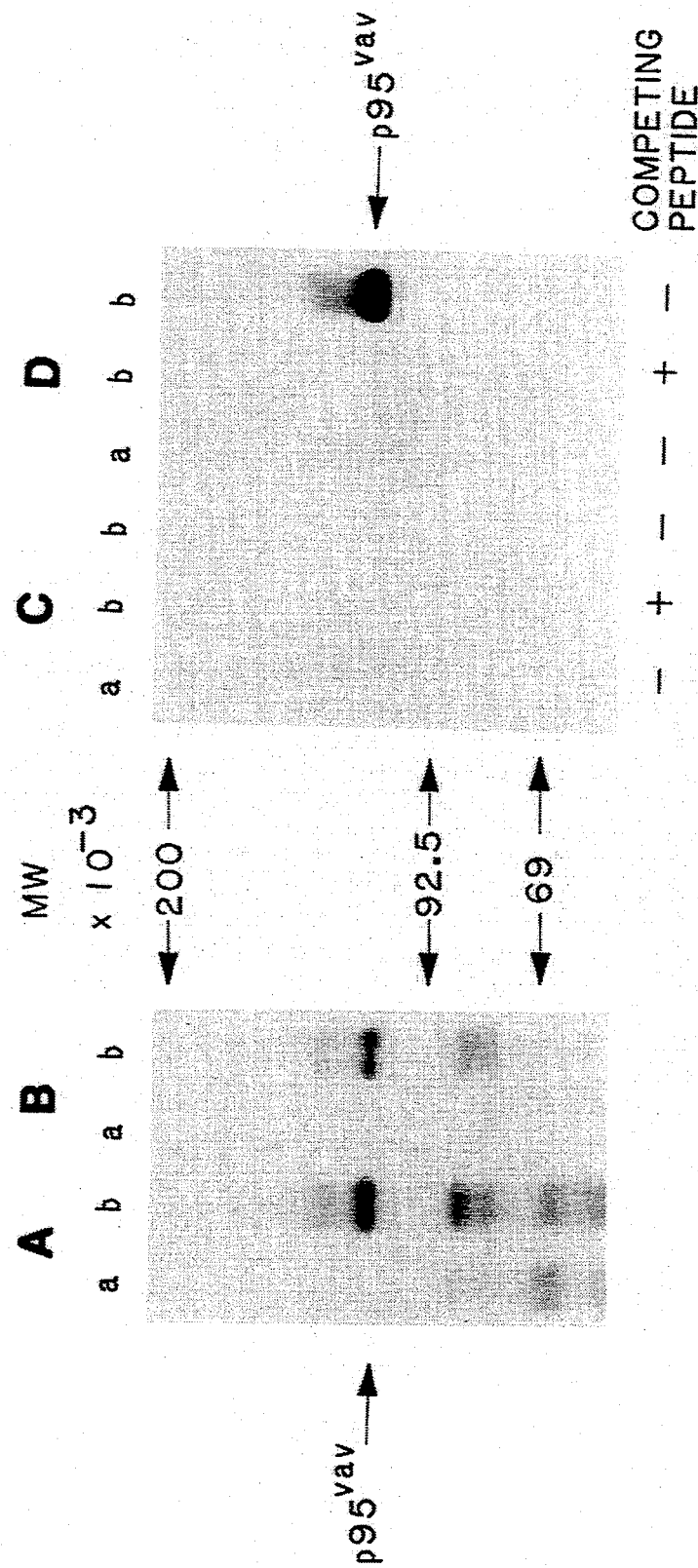
FIG. 4 shows identification of p95$^{vav}$ as a mouse ray proto-oncogene product. [$^{35}$S methionine]-labeled cell extracts of (A) PAb 280, a mouse B-cell hybridoma; (B) PMMS, a mouse T-cell hybridoma; (C) NIH3T3 cells and (D) NIH3T3 cells transfected with pJC13, a pMEX-derived expression plasmid carrying a mouse vav proto-oncogene cDNA clone, were immunoprecipitated with (a) preimmune rabbit serum or (b) an antiserum raised against a peptide corresponding to a hydrophilic domain (amino acid residues 576–589) of a mouse vav protein either in the absence (−) or in the presence (+) of 10 μg of competing peptide. Immunoprecipitates were loaded onto 8% SDS-polyacrylamide gels. Electrophoresed gels were exposed to Kodak X-OMAT film for 2 days at −70° C. in the presence of intensifier screens. The migration of p95$^{vav}$ is indicated by a thick arrow. The migration of co-electrophoresed molecular weight standards including myosin (200,000), phosphorylase B (92,500) and bovine serum albumin (69,000) is also indicated.

[a]See legend to FIG. 4 for experimental details.
[b]Baumbach, W.R. et al., Mol. Cell. Biol. 7, 664–671 (1987)
[c]Coppola, J.A. and Cole, M.D., Nature 320, 760–763 (1986)
[d]Jainchill, J.L. et al., J. Virol. 4, 549–553 (1969)
[e]Mann, R. et al., Cell 33, 153–159 (1983)

TABLE 2

Contribution of the cysteine-rich sequences to the Biological activity of vav gene proteins

| PLASMID | SPECIES | CYSTEINE MOTIF[a] | TRANSFORMING (ffu/μg DNA[b]) |
|---|---|---|---|
| pJC12 | Mouse | $CX_2CX_{13}CX_2CX_4HX_2CX_6CX_2H$ | 450 |
| pJC17 | Mouse | $\underline{S}X_2CX_{13}CX_2CX_4HX_2CX_6CX_2H$ | 0 |
| pJC18 | Mouse | $CX_2CX_{13}\underline{S}X_2CX_4HX_2CX_6CX_2H$ | 0 |
| pJC19 | Mouse | $CX_2CX_{13}CX_2CX_4\underline{D}X_2CX_6CX_2H$ | 0 |
| pJC5 | Human | $CX_2CX_{13}CX_2CX_4HX_2CX_6CX_2H$ | 5,000 |
| pJC15 | Human | $\underline{R}X_2CX_{13}CX_2CX_4HX_2CX_6CX_2H$ | 0 |

[a]Cysteine motifs (residues 528 to 566) contain metal binding-like domains (Cys—$X_2$[SEQ. ID. NO. 4]—Cys—$X_{13}$—Cys—$X_2$—Cys and His—$X_2$—Cys—$X_6$—Cys—$X_6$—Cys—$X_2$—His [SEQ. ID. NO. 5]) and putative phorbol ester binding regions (Cys—$X_2$—Cys—$X_{13}$—Cys—$X_2$—Cys—$X_6$—Cys [SEQ. NO. 8]). Substituted amino acid residues are bolded and underlined.
[b]pSK27 DNA (see FIG. 6) used as positive control in this experiment yielded 5,000 ffu/μg DNA.

---

What is claimed is:

1. An isolated nucleic acid molecule consisting of nucleic acid sequence coding for a mouse vav proto-oncogene protein having the sequence of SEQ ID NO: 2.

2. The nucleic acid molecule according to claim 1 which is a DNA molecule and wherein the nucleic acid sequence is a DNA sequence.

3. The DNA molecule according to claim 2 wherein the DNA sequence has the nucleic acid sequence of SEQ. ID. NO.: 1.

4. A DNA molecule having a DNA sequence which is fully complementary to the DNA sequence according to claim 3.

5. An expression vector comprising a DNA sequence coding for a mouse vav proto-oncogene protein having the sequence of SEQ ID NO: 2.

6. The expression vector according to claim 5 comprising one or more control DNA sequences capable of directing the replication and/or the expression of and operatively linked to the DNA sequence coding for a mouse vav proto-oncogene protein having the sequence of SEQ ID NO: 2.

7. The expression vector according to claim 5 wherein the DNA sequence coding for a mouse vav proto-oncogene protein has the nucleic acid sequence of SEQ. ID. NO.: 1.

8. The expression vector according to claim 5 designated pMB24.

9. A prokaryotic or eukaryotic host cell containing the expression vector according to claim 5.

10. A prokaryotic or eukaryotic host cell containing the expression vector according to claims 6, 7, or 8.

11. A method for producing a polypeptide molecule which comprises a mouse vav proto-oncogene protein having the sequence of SEQ ID NO: 2 comprising culturing a host cell according to claim 9 under conditions permitting expression of the polypeptide molecule.

* * * * *

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 2793 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i x ) FEATURE:
        ( A ) NAME/KEY: CDS
        ( B ) LOCATION: 14..2545

( x i ) SEQUENCE DESCRIPTION: SEQ ID NO:1:

```
GCCGGCAGCC ACC ATG GAG CTC TGG CGA CAG TGC ACC CAC TGG CTG ATC        4 9
            Met Glu Leu Trp Arg Gln Cys Thr His Trp Leu Ile
            1           5                   10
```

| | | | | | | | | | | | | | | | | |
|---|---|---|---|---|---|---|---|---|---|---|---|---|---|---|---|---|
| CAG | TGT | CGG | GTG | CTG | CCT | CCC | AGC | CAC | CGT | GTG | ACC | TGG | GAG | GGG | GCC | 97 |
| Gln | Cys | Arg | Val | Leu | Pro | Pro | Ser | His | Arg | Val | Thr | Trp | Glu | Gly | Ala | |
| | | 15 | | | | | 20 | | | | | 25 | | | | |
| CAG | GTG | TGT | GAG | CTG | GCA | CAG | GCA | CTG | CGG | GAC | GGT | GTC | CTC | TTG | TGC | 145 |
| Gln | Val | Cys | Glu | Leu | Ala | Gln | Ala | Leu | Arg | Asp | Gly | Val | Leu | Leu | Cys | |
| | 30 | | | | | 35 | | | | | 40 | | | | | |
| CAA | TTG | CTT | AAC | AAC | CTG | CTT | CCC | CAG | GCC | ATT | AAT | CTT | CGC | GAG | GTT | 193 |
| Gln | Leu | Leu | Asn | Asn | Leu | Leu | Pro | Gln | Ala | Ile | Asn | Leu | Arg | Glu | Val | |
| 45 | | | | | 50 | | | | | 55 | | | | | 60 | |
| AAC | TTG | CGG | CCC | CAG | ATG | TCC | CAG | TTC | CTT | TGT | CTT | AAG | AAC | ATT | CGA | 241 |
| Asn | Leu | Arg | Pro | Gln | Met | Ser | Gln | Phe | Leu | Cys | Leu | Lys | Asn | Ile | Arg | |
| | | | | 65 | | | | | 70 | | | | | 75 | | |
| ACC | TTC | CTG | TCT | ACT | TGC | TGT | GAG | AAG | TTC | GGC | CTC | AAG | CGC | AGT | GAA | 289 |
| Thr | Phe | Leu | Ser | Thr | Cys | Cys | Glu | Lys | Phe | Gly | Leu | Lys | Arg | Ser | Glu | |
| | | | 80 | | | | | 85 | | | | | 90 | | | |
| CTC | TTT | GAG | GCT | TTT | GAC | CTC | TTC | GAT | GTG | CAG | GAC | TTT | GGA | AAG | GTC | 337 |
| Leu | Phe | Glu | Ala | Phe | Asp | Leu | Phe | Asp | Val | Gln | Asp | Phe | Gly | Lys | Val | |
| | | 95 | | | | | 100 | | | | | 105 | | | | |
| ATC | TAC | ACC | CTG | TCT | GCT | CTG | TCA | TGG | ACA | CCC | ATT | GCC | CAG | AAC | AAA | 385 |
| Ile | Tyr | Thr | Leu | Ser | Ala | Leu | Ser | Trp | Thr | Pro | Ile | Ala | Gln | Asn | Lys | |
| | | 110 | | | | | 115 | | | | | 120 | | | | |
| GGA | ATC | ATG | CCC | TTC | CCA | ACA | GAG | GAC | AGC | GCT | CTG | AAC | GAC | GAA | GAT | 433 |
| Gly | Ile | Met | Pro | Phe | Pro | Thr | Glu | Asp | Ser | Ala | Leu | Asn | Asp | Glu | Asp | |
| 125 | | | | | 130 | | | | | 135 | | | | | 140 | |
| ATT | TAC | AGT | GGC | CTT | TCA | GAC | CAG | ATT | GAT | GAC | ACC | GCA | GAG | GAA | GAC | 481 |
| Ile | Tyr | Ser | Gly | Leu | Ser | Asp | Gln | Ile | Asp | Asp | Thr | Ala | Glu | Glu | Asp | |
| | | | | 145 | | | | | 150 | | | | | | 155 | |
| GAG | GAC | CTT | TAT | GAC | TGC | GTG | GAA | AAT | GAG | GAG | GCA | GAG | GGG | GAC | GAG | 529 |
| Glu | Asp | Leu | Tyr | Asp | Cys | Val | Glu | Asn | Glu | Glu | Ala | Glu | Gly | Asp | Glu | |
| | | | 160 | | | | | 165 | | | | | 170 | | | |
| ATC | TAC | GAG | GAC | CTA | ATG | CGC | TTG | GAG | TCG | GTG | CCT | ACG | CCA | CCC | AAG | 577 |
| Ile | Tyr | Glu | Asp | Leu | Met | Arg | Leu | Glu | Ser | Val | Pro | Thr | Pro | Pro | Lys | |
| | | 175 | | | | | 180 | | | | | 185 | | | | |
| ATG | ACA | GAG | TAT | GAT | AAG | CGC | TGC | TGC | TGC | CTG | CGG | GAG | ATC | CAG | CAG | 625 |
| Met | Thr | Glu | Tyr | Asp | Lys | Arg | Cys | Cys | Cys | Leu | Arg | Glu | Ile | Gln | Gln | |
| | 190 | | | | | 195 | | | | | 200 | | | | | |
| ACG | GAG | GAG | AAG | TAT | ACA | GAC | ACA | CTG | GGC | TCC | ATC | CAG | CAG | CAC | TTC | 673 |
| Thr | Glu | Glu | Lys | Tyr | Thr | Asp | Thr | Leu | Gly | Ser | Ile | Gln | Gln | His | Phe | |
| 205 | | | | | 210 | | | | | 215 | | | | | 220 | |
| ATG | AAG | CCT | CTG | CAG | CGA | TTC | CTT | AAG | CCT | CAA | GAC | ATG | GAG | ACC | ATC | 721 |
| Met | Lys | Pro | Leu | Gln | Arg | Phe | Leu | Lys | Pro | Gln | Asp | Met | Glu | Thr | Ile | |
| | | | | 225 | | | | | 230 | | | | | 235 | | |
| TTT | GTC | AAC | ATT | GAG | GAG | CTG | TTC | TCT | GTG | CAT | ACC | CAC | TTC | TTA | AAG | 769 |
| Phe | Val | Asn | Ile | Glu | Glu | Leu | Phe | Ser | Val | His | Thr | His | Phe | Leu | Lys | |
| | | | 240 | | | | | 245 | | | | | 250 | | | |
| GAA | CTG | AAG | GAT | GCC | CTG | GCT | GGC | CCG | GGA | GCA | ACA | ACA | CTG | TAT | CAG | 817 |
| Glu | Leu | Lys | Asp | Ala | Leu | Ala | Gly | Pro | Gly | Ala | Thr | Thr | Leu | Tyr | Gln | |
| | | 255 | | | | | 260 | | | | | 265 | | | | |
| GTC | TTC | ATC | AAG | TAC | AAG | GAG | AGG | TTC | CTG | GTT | TAT | GGC | CGT | TAT | TGC | 865 |
| Val | Phe | Ile | Lys | Tyr | Lys | Glu | Arg | Phe | Leu | Val | Tyr | Gly | Arg | Tyr | Cys | |
| | 270 | | | | | 275 | | | | | 280 | | | | | |
| AGT | CAG | GTG | GAG | TCA | GCC | AGC | AAG | CAC | TTG | GAT | CAA | GTG | GCC | ACA | GCA | 913 |
| Ser | Gln | Val | Glu | Ser | Ala | Ser | Lys | His | Leu | Asp | Gln | Val | Ala | Thr | Ala | |
| 285 | | | | | 290 | | | | | 295 | | | | | 300 | |
| CGG | GAG | GAT | GTG | CAG | ATG | AAG | CTG | GAG | GAA | TGT | TCT | CAA | AGA | GCT | AAC | 961 |
| Arg | Glu | Asp | Val | Gln | Met | Lys | Leu | Glu | Glu | Cys | Ser | Gln | Arg | Ala | Asn | |
| | | | | 305 | | | | | 310 | | | | | 315 | | |
| AAT | GGC | CGA | TTC | ACC | CTA | CGG | TCT | GCT | GAT | GGT | ACC | TAT | GCA | GCG | GGT | 1009 |
| Asn | Gly | Arg | Phe | Thr | Leu | Arg | Ser | Ala | Asp | Gly | Thr | Tyr | Ala | Ala | Gly | |
| | | | 320 | | | | | 325 | | | | | 330 | | | |
| GCT | GAA | GTA | CCA | CCT | CCT | TCT | CCA | GGA | GCT | AGT | GAA | ACA | CAC | ACA | GGA | 1057 |
| Ala | Glu | Val | Pro | Pro | Pro | Ser | Pro | Gly | Ala | Ser | Glu | Thr | His | Thr | Gly | |

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
|     |     | 335 |     |     |     |     | 340 |     |     |     |     | 345 |     |     |     |     |
| TGC | TAC | AGA | GAA | GGA | GAA | CTG | CGG | TTG | GCC | CTG | GAC | GCC | ATG | AGG | GAC | 1105 |
| Cys | Tyr | Arg | Glu | Gly | Glu | Leu | Arg | Leu | Ala | Leu | Asp | Ala | Met | Arg | Asp |      |
|     | 350 |     |     |     | 355 |     |     |     |     | 360 |     |     |     |     |     |      |
| CTG | GCA | CAG | TGC | GTG | AAC | GAG | GTC | AAG | AGG | GAC | AAT | GAA | ACC | CTA | CGG | 1153 |
| Leu | Ala | Gln | Cys | Val | Asn | Glu | Val | Lys | Arg | Asp | Asn | Glu | Thr | Leu | Arg |      |
| 365 |     |     |     | 370 |     |     |     |     | 375 |     |     |     |     |     | 380 |      |
| CAG | ATC | ACA | AAC | TTT | CAG | CTG | TCC | ATT | GAG | AAC | CTG | GAC | CAG | TCT | CTG | 1201 |
| Gln | Ile | Thr | Asn | Phe | Gln | Leu | Ser | Ile | Glu | Asn | Leu | Asp | Gln | Ser | Leu |      |
|     |     |     |     | 385 |     |     |     |     | 390 |     |     |     |     | 395 |     |      |
| GCT | AAC | TAT | GGC | CGG | CCC | AAG | ATT | GAC | GGT | GAG | CTC | AAG | ATT | ACC | TCA | 1249 |
| Ala | Asn | Tyr | Gly | Arg | Pro | Lys | Ile | Asp | Gly | Glu | Leu | Lys | Ile | Thr | Ser |      |
|     |     |     | 400 |     |     |     |     | 405 |     |     |     |     | 410 |     |     |      |
| GTG | GAG | CGT | CGC | TCA | AAG | ACA | GAC | AGG | TAT | GCC | TTC | CTG | CTG | GAC | AAA | 1297 |
| Val | Glu | Arg | Arg | Ser | Lys | Thr | Asp | Arg | Tyr | Ala | Phe | Leu | Leu | Asp | Lys |      |
|     |     | 415 |     |     |     |     | 420 |     |     |     |     | 425 |     |     |     |      |
| GCA | CTG | CTC | ATC | TGT | AAA | CGC | CGC | GGG | GAC | TCT | TAC | GAC | CTC | AAA | GCC | 1345 |
| Ala | Leu | Leu | Ile | Cys | Lys | Arg | Arg | Gly | Asp | Ser | Tyr | Asp | Leu | Lys | Ala |      |
|     | 430 |     |     |     |     | 435 |     |     |     |     | 440 |     |     |     |     |      |
| TCG | GTG | AAC | TTG | CAC | AGC | TTC | CAA | GTT | TCA | GAT | GAC | TCC | TCC | GGG | GAG | 1393 |
| Ser | Val | Asn | Leu | His | Ser | Phe | Gln | Val | Ser | Asp | Asp | Ser | Ser | Gly | Glu |      |
| 445 |     |     |     |     | 450 |     |     |     |     | 455 |     |     |     |     | 460 |      |
| CGA | GAC | AAC | AAG | AAG | TGG | AGC | CAT | ATG | TTC | CTT | CTG | ATT | GAG | GAT | CAA | 1441 |
| Arg | Asp | Asn | Lys | Lys | Trp | Ser | His | Met | Phe | Leu | Leu | Ile | Glu | Asp | Gln |      |
|     |     |     |     | 465 |     |     |     |     | 470 |     |     |     |     | 475 |     |      |
| GGC | GCC | CAG | GGC | TAT | GAG | CTG | TTC | TTC | AAG | ACT | CGG | GAG | CTG | AAG | AAG | 1489 |
| Gly | Ala | Gln | Gly | Tyr | Glu | Leu | Phe | Phe | Lys | Thr | Arg | Glu | Leu | Lys | Lys |      |
|     |     |     | 480 |     |     |     |     | 485 |     |     |     |     | 490 |     |     |      |
| AAG | TGG | ATG | GAA | CAG | TTC | GAA | ATG | GCC | ATC | TCC | AAC | ATT | TAC | CCA | GAG | 1537 |
| Lys | Trp | Met | Glu | Gln | Phe | Glu | Met | Ala | Ile | Ser | Asn | Ile | Tyr | Pro | Glu |      |
|     |     | 495 |     |     |     |     | 500 |     |     |     |     | 505 |     |     |     |      |
| AAT | GCT | ACA | GCC | AAT | GGG | CAT | GAT | TTT | CAG | ATG | TTC | TCC | TTT | GAG | GAG | 1585 |
| Asn | Ala | Thr | Ala | Asn | Gly | His | Asp | Phe | Gln | Met | Phe | Ser | Phe | Glu | Glu |      |
|     | 510 |     |     |     |     | 515 |     |     |     |     | 520 |     |     |     |     |      |
| ACC | ACT | TCC | TGC | AAG | GCC | TGC | CAG | ATG | TTA | CTC | AGA | GGC | ACA | TTC | TAC | 1633 |
| Thr | Thr | Ser | Cys | Lys | Ala | Cys | Gln | Met | Leu | Leu | Arg | Gly | Thr | Phe | Tyr |      |
| 525 |     |     |     |     | 530 |     |     |     |     | 535 |     |     |     |     | 540 |      |
| CAG | GGA | TAT | CGC | TGT | TAC | AGG | TGC | CGG | GCA | CCT | GCA | CAC | AAG | GAG | TGT | 1681 |
| Gln | Gly | Tyr | Arg | Cys | Tyr | Arg | Cys | Arg | Ala | Pro | Ala | His | Lys | Glu | Cys |      |
|     |     |     |     | 545 |     |     |     |     | 550 |     |     |     |     | 555 |     |      |
| CTG | GGG | AGA | GTG | CCT | CCC | TGT | GGT | CGC | CAT | GGG | CAA | GAT | TTC | GCA | GGA | 1729 |
| Leu | Gly | Arg | Val | Pro | Pro | Cys | Gly | Arg | His | Gly | Gln | Asp | Phe | Ala | Gly |      |
|     |     |     | 560 |     |     |     |     | 565 |     |     |     |     | 570 |     |     |      |
| ACC | ATG | AAG | AAG | GAC | AAG | CTC | CAT | CGA | AGG | GCC | CAG | GAC | AAG | AAA | AGG | 1777 |
| Thr | Met | Lys | Lys | Asp | Lys | Leu | His | Arg | Arg | Ala | Gln | Asp | Lys | Lys | Arg |      |
|     |     | 575 |     |     |     |     | 580 |     |     |     |     | 585 |     |     |     |      |
| AAT | GAA | TTG | GGT | CTG | CCT | AAG | ATG | GAA | GTG | TTT | CAG | GAA | TAC | TAT | GGG | 1825 |
| Asn | Glu | Leu | Gly | Leu | Pro | Lys | Met | Glu | Val | Phe | Gln | Glu | Tyr | Tyr | Gly |      |
|     | 590 |     |     |     |     | 595 |     |     |     |     | 600 |     |     |     |     |      |
| ATC | CCA | CCA | CCA | CCT | GGA | GCC | TTT | GGG | CCA | TTT | TTA | CGG | CTC | AAC | CCT | 1873 |
| Ile | Pro | Pro | Pro | Pro | Gly | Ala | Phe | Gly | Pro | Phe | Leu | Arg | Leu | Asn | Pro |      |
| 605 |     |     |     |     | 610 |     |     |     |     | 615 |     |     |     |     | 620 |      |
| GGG | GAC | ATT | GTG | GAG | CTC | ACT | AAG | GCA | GAG | GCT | GAG | CAC | AAC | TGG | TGG | 1921 |
| Gly | Asp | Ile | Val | Glu | Leu | Thr | Lys | Ala | Glu | Ala | Glu | His | Asn | Trp | Trp |      |
|     |     |     |     | 625 |     |     |     |     | 630 |     |     |     |     | 635 |     |      |
| GAG | GGA | AGG | AAT | ACT | GCT | ACA | AAT | GAA | GTC | GGC | TGG | TTT | CCC | TGT | AAC | 1969 |
| Glu | Gly | Arg | Asn | Thr | Ala | Thr | Asn | Glu | Val | Gly | Trp | Phe | Pro | Cys | Asn |      |
|     |     |     | 640 |     |     |     |     | 645 |     |     |     |     | 650 |     |     |      |
| AGA | GTG | CAT | CCC | TAT | GTC | CAC | GGC | CCT | CCT | CAG | GAC | CTG | TCT | GTG | CAT | 2017 |
| Arg | Val | His | Pro | Tyr | Val | His | Gly | Pro | Pro | Gln | Asp | Leu | Ser | Val | His |      |
|     |     | 655 |     |     |     |     | 660 |     |     |     |     | 665 |     |     |     |      |

-continued

| | | | | | | | | | | | | | | | | |
|---|---|---|---|---|---|---|---|---|---|---|---|---|---|---|---|---|
| CTC | TGG | TAT | GCG | GGC | CCT | ATG | GAA | CGA | GCA | GGC | GCT | GAG | GGC | ATC | CTC | 2065 |
| Leu | Trp | Tyr | Ala | Gly | Pro | Met | Glu | Arg | Ala | Gly | Ala | Glu | Gly | Ile | Leu | |
| | 670 | | | | | 675 | | | | | 680 | | | | | |
| ACC | AAC | CGT | TCT | GAT | GGG | ACC | TAT | CTG | GTG | CGG | CAG | AGG | GTG | AAA | GAT | 2113 |
| Thr | Asn | Arg | Ser | Asp | Gly | Thr | Tyr | Leu | Val | Arg | Gln | Arg | Val | Lys | Asp | |
| 685 | | | | | 690 | | | | | 695 | | | | | 700 | |
| ACA | GCG | GAG | TTC | GCC | ATC | AGC | ATT | AAG | TAT | AAC | GTG | GAG | GTC | AAG | CAT | 2161 |
| Thr | Ala | Glu | Phe | Ala | Ile | Ser | Ile | Lys | Tyr | Asn | Val | Glu | Val | Lys | His | |
| | | | | 705 | | | | | 710 | | | | | 715 | | |
| ATT | AAA | ATC | ATG | ACG | TCA | GAG | GGG | TTG | TAC | CGG | ATC | ACA | GAG | AAG | AAG | 2209 |
| Ile | Lys | Ile | Met | Thr | Ser | Glu | Gly | Leu | Tyr | Arg | Ile | Thr | Glu | Lys | Lys | |
| | | | 720 | | | | | 725 | | | | | 730 | | | |
| GCT | TTC | CGG | GGC | CTT | CTG | GAA | CTG | GTA | GAG | TTT | TAT | CAG | CAG | AAT | TCC | 2257 |
| Ala | Phe | Arg | Gly | Leu | Leu | Glu | Leu | Val | Glu | Phe | Tyr | Gln | Gln | Asn | Ser | |
| | | 735 | | | | | 740 | | | | | 745 | | | | |
| CTC | AAA | GAT | TGC | TTC | AAG | TCG | TTG | GAC | ACC | ACC | TTG | CAG | TTT | CCT | TAT | 2305 |
| Leu | Lys | Asp | Cys | Phe | Lys | Ser | Leu | Asp | Thr | Thr | Leu | Gln | Phe | Pro | Tyr | |
| | 750 | | | | | 755 | | | | | 760 | | | | | |
| AAG | GAA | CCT | GAG | AGG | AGA | GCC | ATC | AGC | AAG | CCA | CCA | GCT | GGA | AGC | ACC | 2353 |
| Lys | Glu | Pro | Glu | Arg | Arg | Ala | Ile | Ser | Lys | Pro | Pro | Ala | Gly | Ser | Thr | |
| 765 | | | | | 770 | | | | | 775 | | | | | 780 | |
| AAG | TAT | TTT | GGC | ACT | GCC | AAA | GCC | CGC | TAC | GAC | TTC | TGT | GCC | CGG | GAC | 2401 |
| Lys | Tyr | Phe | Gly | Thr | Ala | Lys | Ala | Arg | Tyr | Asp | Phe | Cys | Ala | Arg | Asp | |
| | | | | 785 | | | | | 790 | | | | | 795 | | |
| AGG | TCG | GAA | CTG | TCC | CTT | AAG | GAG | GGT | GAT | ATC | ATC | AAG | ATC | CTC | AAT | 2449 |
| Arg | Ser | Glu | Leu | Ser | Leu | Lys | Glu | Gly | Asp | Ile | Ile | Lys | Ile | Leu | Asn | |
| | | | 800 | | | | | 805 | | | | | 810 | | | |
| AAG | AAG | GGA | CAG | CAA | GGC | TGG | TGG | CGT | GGG | GAG | ATC | TAC | GGC | CGG | ATC | 2497 |
| Lys | Lys | Gly | Gln | Gln | Gly | Trp | Trp | Arg | Gly | Glu | Ile | Tyr | Gly | Arg | Ile | |
| | | 815 | | | | | 820 | | | | | 825 | | | | |
| GGC | TGG | TTC | CCT | TCT | AAC | TAT | GTG | GAG | GAA | GAC | TAT | TCC | GAA | TAT | TGC | 2545 |
| Gly | Trp | Phe | Pro | Ser | Asn | Tyr | Val | Glu | Glu | Asp | Tyr | Ser | Glu | Tyr | Cys | |
| | 830 | | | | | 835 | | | | | 840 | | | | | |

| | | | | |
|---|---|---|---|---|
| TGAGCCTGGT | GCCCTGTAGG | ACACAGAGAG | AGGCAGATGA | AGGCTGAGCC CAGGATGCTA | 2605 |
| GCAGGGTTGA | GGGGCCATGA | ACTGTCCTCA | CCACGGAGGA | TCTGGATGCG TGCAGATGGC | 2665 |
| TAGTGGCCAG | CTGGCAGGGT | TCCCAGGATA | AAGCCCAGAG | ATGCGTAATT TATAACACAC | 2725 |
| TGATTTTCTC | CAGTCCTCCA | CGAAAGGTGG | GGCTTGAGGC | AACTGATTCT AATAAAGTGA | 2785 |
| GGAGAGCA | | | | | 2793 |

( 2 ) INFORMATION FOR SEQ ID NO:2:

( i ) SEQUENCE CHARACTERISTICS:
        ( A ) LENGTH: 844 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | | |
|---|---|---|---|---|---|---|---|---|---|---|---|---|---|---|---|
| Met | Glu | Leu | Trp | Arg | Gln | Cys | Thr | His | Trp | Leu | Ile | Gln | Cys | Arg | Val |
| 1 | | | | 5 | | | | | 10 | | | | | 15 | |
| Leu | Pro | Pro | Ser | His | Arg | Val | Thr | Trp | Glu | Gly | Ala | Gln | Val | Cys | Glu |
| | | | 20 | | | | | 25 | | | | | 30 | | |
| Leu | Ala | Gln | Ala | Leu | Arg | Asp | Gly | Val | Leu | Leu | Cys | Gln | Leu | Leu | Asn |
| | | 35 | | | | | 40 | | | | | 45 | | | |
| Asn | Leu | Leu | Pro | Gln | Ala | Ile | Asn | Leu | Arg | Glu | Val | Asn | Leu | Arg | Pro |
| | 50 | | | | | 55 | | | | | 60 | | | | |
| Gln | Met | Ser | Gln | Phe | Leu | Cys | Leu | Lys | Asn | Ile | Arg | Thr | Phe | Leu | Ser |
| 65 | | | | | 70 | | | | | 75 | | | | | 80 |
| Thr | Cys | Cys | Glu | Lys | Phe | Gly | Leu | Lys | Arg | Ser | Glu | Leu | Phe | Glu | Ala |

|    |    |    |    |    | 85  |    |    |    | 90  |    |    |    |    | 95  |    |
|----|----|----|----|----|-----|----|----|----|-----|----|----|----|----|-----|----|
| Phe | Asp | Leu | Phe | Asp | Val | Gln | Asp | Phe | Gly | Lys | Val | Ile | Tyr | Thr | Leu |
|     |     |     | 100 |     |     |     | 105 |     |     |     | 110 |     |     |     |     |
| Ser | Ala | Leu | Ser | Trp | Thr | Pro | Ile | Ala | Gln | Asn | Lys | Gly | Ile | Met | Pro |
|     |     | 115 |     |     |     | 120 |     |     |     |     | 125 |     |     |     |     |
| Phe | Pro | Thr | Glu | Asp | Ser | Ala | Leu | Asn | Asp | Glu | Asp | Ile | Tyr | Ser | Gly |
|     | 130 |     |     |     |     | 135 |     |     |     | 140 |     |     |     |     |     |
| Leu | Ser | Asp | Gln | Ile | Asp | Asp | Thr | Ala | Glu | Glu | Asp | Glu | Asp | Leu | Tyr |
| 145 |     |     |     | 150 |     |     |     |     | 155 |     |     |     |     |     | 160 |
| Asp | Cys | Val | Glu | Asn | Glu | Glu | Ala | Glu | Gly | Asp | Glu | Ile | Tyr | Glu | Asp |
|     |     |     |     | 165 |     |     |     |     | 170 |     |     |     | 175 |     |     |
| Leu | Met | Arg | Leu | Glu | Ser | Val | Pro | Thr | Pro | Pro | Lys | Met | Thr | Glu | Tyr |
|     |     |     | 180 |     |     |     |     | 185 |     |     |     |     | 190 |     |     |
| Asp | Lys | Arg | Cys | Cys | Cys | Leu | Arg | Glu | Ile | Gln | Gln | Thr | Glu | Glu | Lys |
|     |     | 195 |     |     |     |     | 200 |     |     |     |     | 205 |     |     |     |
| Tyr | Thr | Asp | Thr | Leu | Gly | Ser | Ile | Gln | Gln | His | Phe | Met | Lys | Pro | Leu |
| 210 |     |     |     |     |     | 215 |     |     |     |     | 220 |     |     |     |     |
| Gln | Arg | Phe | Leu | Lys | Pro | Gln | Asp | Met | Glu | Thr | Ile | Phe | Val | Asn | Ile |
| 225 |     |     |     |     | 230 |     |     |     |     | 235 |     |     |     |     | 240 |
| Glu | Glu | Leu | Phe | Ser | Val | His | Thr | His | Phe | Leu | Lys | Glu | Leu | Lys | Asp |
|     |     |     |     | 245 |     |     |     |     | 250 |     |     |     | 255 |     |     |
| Ala | Leu | Ala | Gly | Pro | Gly | Ala | Thr | Thr | Leu | Tyr | Gln | Val | Phe | Ile | Lys |
|     |     |     | 260 |     |     |     |     | 265 |     |     |     |     | 270 |     |     |
| Tyr | Lys | Glu | Arg | Phe | Leu | Val | Tyr | Gly | Arg | Tyr | Cys | Ser | Gln | Val | Glu |
|     |     | 275 |     |     |     |     | 280 |     |     |     |     | 285 |     |     |     |
| Ser | Ala | Ser | Lys | His | Leu | Asp | Gln | Val | Ala | Thr | Ala | Arg | Glu | Asp | Val |
|     | 290 |     |     |     |     | 295 |     |     |     |     | 300 |     |     |     |     |
| Gln | Met | Lys | Leu | Glu | Glu | Cys | Ser | Gln | Arg | Ala | Asn | Asn | Gly | Arg | Phe |
| 305 |     |     |     |     | 310 |     |     |     |     | 315 |     |     |     |     | 320 |
| Thr | Leu | Arg | Ser | Ala | Asp | Gly | Thr | Tyr | Ala | Ala | Gly | Ala | Glu | Val | Pro |
|     |     |     |     | 325 |     |     |     |     | 330 |     |     |     |     | 335 |     |
| Pro | Pro | Ser | Pro | Gly | Ala | Ser | Glu | Thr | His | Thr | Gly | Cys | Tyr | Arg | Glu |
|     |     |     | 340 |     |     |     |     | 345 |     |     |     |     | 350 |     |     |
| Gly | Glu | Leu | Arg | Leu | Ala | Leu | Asp | Ala | Met | Arg | Asp | Leu | Ala | Gln | Cys |
|     |     |     | 355 |     |     |     |     | 360 |     |     |     | 365 |     |     |     |
| Val | Asn | Glu | Val | Lys | Arg | Asp | Asn | Glu | Thr | Leu | Arg | Gln | Ile | Thr | Asn |
| 370 |     |     |     |     |     | 375 |     |     |     |     | 380 |     |     |     |     |
| Phe | Gln | Leu | Ser | Ile | Glu | Asn | Leu | Asp | Gln | Ser | Leu | Ala | Asn | Tyr | Gly |
| 385 |     |     |     |     | 390 |     |     |     |     | 395 |     |     |     |     | 400 |
| Arg | Pro | Lys | Ile | Asp | Gly | Glu | Leu | Lys | Ile | Thr | Ser | Val | Glu | Arg | Arg |
|     |     |     |     | 405 |     |     |     |     | 410 |     |     |     |     | 415 |     |
| Ser | Lys | Thr | Asp | Arg | Tyr | Ala | Phe | Leu | Leu | Asp | Lys | Ala | Leu | Leu | Ile |
|     |     |     | 420 |     |     |     |     | 425 |     |     |     |     | 430 |     |     |
| Cys | Lys | Arg | Arg | Gly | Asp | Ser | Tyr | Asp | Leu | Lys | Ala | Ser | Val | Asn | Leu |
|     |     | 435 |     |     |     |     | 440 |     |     |     |     | 445 |     |     |     |
| His | Ser | Phe | Gln | Val | Ser | Asp | Ser | Ser | Gly | Glu | Arg | Asp | Asn | Lys |     |
|     | 450 |     |     |     |     | 455 |     |     |     |     | 460 |     |     |     |     |
| Lys | Trp | Ser | His | Met | Phe | Leu | Leu | Ile | Glu | Asp | Gln | Gly | Ala | Gln | Gly |
| 465 |     |     |     |     | 470 |     |     |     |     | 475 |     |     |     |     | 480 |
| Tyr | Glu | Leu | Phe | Phe | Lys | Thr | Arg | Glu | Leu | Lys | Lys | Lys | Trp | Met | Glu |
|     |     |     |     | 485 |     |     |     |     | 490 |     |     |     |     | 495 |     |
| Gln | Phe | Glu | Met | Ala | Ile | Ser | Asn | Ile | Tyr | Pro | Glu | Asn | Ala | Thr | Ala |
|     |     |     |     | 500 |     |     |     |     | 505 |     |     |     |     | 510 |     |
| Asn | Gly | His | Asp | Phe | Gln | Met | Phe | Ser | Phe | Glu | Glu | Thr | Thr | Ser | Cys |
|     |     | 515 |     |     |     |     | 520 |     |     |     |     | 525 |     |     |     |

```
Lys Ala Cys Gln Met Leu Leu Arg Gly Thr Phe Tyr Gln Gly Tyr Arg
    530                 535                 540

Cys Tyr Arg Cys Arg Ala Pro Ala His Lys Glu Cys Leu Gly Arg Val
545                 550                 555                 560

Pro Pro Cys Gly Arg His Gly Gln Asp Phe Ala Gly Thr Met Lys Lys
            565                 570                 575

Asp Lys Leu His Arg Arg Ala Gln Asp Lys Lys Arg Asn Glu Leu Gly
            580                 585                 590

Leu Pro Lys Met Glu Val Phe Gln Glu Tyr Tyr Gly Ile Pro Pro Pro
        595                 600                 605

Pro Gly Ala Phe Gly Pro Phe Leu Arg Leu Asn Pro Gly Asp Ile Val
    610                 615                 620

Glu Leu Thr Lys Ala Glu Ala His Asn Trp Trp Glu Gly Arg Asn
625                 630                 635                 640

Thr Ala Thr Asn Glu Val Gly Trp Phe Pro Cys Asn Arg Val His Pro
                645                 650                 655

Tyr Val His Gly Pro Pro Gln Asp Leu Ser Val His Leu Trp Tyr Ala
            660                 665                 670

Gly Pro Met Glu Arg Ala Gly Ala Glu Gly Ile Leu Thr Asn Arg Ser
        675                 680                 685

Asp Gly Thr Tyr Leu Val Arg Gln Arg Val Lys Asp Thr Ala Glu Phe
    690                 695                 700

Ala Ile Ser Ile Lys Tyr Asn Val Glu Val Lys His Ile Lys Ile Met
705                 710                 715                 720

Thr Ser Glu Gly Leu Tyr Arg Ile Thr Glu Lys Lys Ala Phe Arg Gly
            725                 730                 735

Leu Leu Glu Leu Val Glu Phe Tyr Gln Gln Asn Ser Leu Lys Asp Cys
        740                 745                 750

Phe Lys Ser Leu Asp Thr Thr Leu Gln Phe Pro Tyr Lys Glu Pro Glu
    755                 760                 765

Arg Arg Ala Ile Ser Lys Pro Pro Ala Gly Ser Thr Lys Tyr Phe Gly
770                 775                 780

Thr Ala Lys Ala Arg Tyr Asp Phe Cys Ala Arg Asp Arg Ser Glu Leu
785                 790                 795                 800

Ser Leu Lys Glu Gly Asp Ile Ile Lys Ile Leu Asn Lys Lys Gly Gln
            805                 810                 815

Gln Gly Trp Trp Arg Gly Glu Ile Tyr Gly Arg Ile Gly Trp Phe Pro
        820                 825                 830

Ser Asn Tyr Val Glu Glu Asp Tyr Ser Glu Tyr Cys
        835                 840
```

( 2 ) INFORMATION FOR SEQ ID NO:3:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

CCGGCTGCAG GCCACCATGG AGCTGTGGCG CCAATGCACC 40

( 2 ) INFORMATION FOR SEQ ID NO:4:

( i ) SEQUENCE CHARACTERISTICS:
        ( A ) LENGTH: 21 amino acids
        ( B ) TYPE: amino acid ( C ) STRANDEDNESS: single
          ( D ) TOPOLOGY: linear ( i i ) MOLECULE TYPE: protein ( x i ) SEQUENCE DESCRIPTION: SEQ ID NO:4:

Cys Xaa Xaa Cys Xaa Xaa Xaa Xaa Xaa Xaa Xaa Xaa Xaa Xaa Xaa
1               5                   10                  15

Xaa Cys Xaa Xaa Cys
         20

( 2 ) INFORMATION FOR SEQ ID NO:5:

( i ) SEQUENCE CHARACTERISTICS:
          ( A ) LENGTH: 14 amino acids
          ( B ) TYPE: amino acid
          ( C ) STRANDEDNESS: single
          ( D ) TOPOLOGY: linear ( i i ) MOLECULE TYPE: protein ( x i ) SEQUENCE DESCRIPTION: SEQ ID NO:5:

His Xaa Xaa Cys Xaa Xaa Xaa Xaa Xaa Xaa Cys Xaa Xaa His
1               5                   10

( 2 ) INFORMATION FOR SEQ ID NO:6:

( i ) SEQUENCE CHARACTERISTICS:
          ( A ) LENGTH: 14 amino acids
          ( B ) TYPE: amino acid
          ( C ) STRANDEDNESS: single
          ( D ) TOPOLOGY: linear ( i i ) MOLECULE TYPE: peptide ( x i ) SEQUENCE DESCRIPTION: SEQ ID NO:6:

Lys Asp Lys Leu His Arg Arg Ala Gln Asp Lys Lys Arg Asn
1               5                   10

( 2 ) INFORMATION FOR SEQ ID NO:7:

( i ) SEQUENCE CHARACTERISTICS:
          ( A ) LENGTH: 10 base pairs
          ( B ) TYPE: nucleic acid
          ( C ) STRANDEDNESS: single
          ( D ) TOPOLOGY: linear ( i i ) MOLECULE TYPE: cDNA ( x i ) SEQUENCE DESCRIPTION: SEQ ID NO:7:

GCCACCATGG                                                                10

( 2 ) INFORMATION FOR SEQ ID NO:8:

( i ) SEQUENCE CHARACTERISTICS:
          ( A ) LENGTH: 31 amino acids
          ( B ) TYPE: amino acid
          ( C ) STRANDEDNESS: single
          ( D ) TOPOLOGY: linear ( i i ) MOLECULE TYPE: protein ( x i ) SEQUENCE DESCRIPTION: SEQ ID NO:8:

Cys Xaa Xaa Cys Xaa Xaa Xaa Xaa Xaa Xaa Xaa Xaa Xaa Xaa Xaa
1               5                   10                  15

Xaa Cys Xaa Xaa Cys Xaa Xaa Xaa Cys Xaa Xaa Xaa Xaa Xaa Cys
         20                  25                  30

( 2 ) INFORMATION FOR SEQ ID NO:9:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:9:

Ala Leu Arg Asp Xaa Val
1               5

( 2 ) INFORMATION FOR SEQ ID NO:10:

( i ) SEQUENCE CHARACTERISTICS:
    ( A ) LENGTH: 38 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:10:

Cys Xaa Xaa Cys Xaa Xaa Xaa Xaa Xaa Xaa Xaa Xaa Xaa Xaa Xaa
1               5                   10                  15

Xaa Cys Xaa Xaa Cys Xaa Xaa Xaa Xaa His Xaa Xaa Cys Xaa Xaa
            20                  25                  30

Xaa Xaa Xaa Cys Xaa Xaa
            35

( 2 ) INFORMATION FOR SEQ ID NO:11:

( i ) SEQUENCE CHARACTERISTICS:
    ( A ) LENGTH: 38 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:11:

Ser Xaa Xaa Cys Xaa Xaa Xaa Xaa Xaa Xaa Xaa Xaa Xaa Xaa Xaa
1               5                   10                  15

Xaa Cys Xaa Xaa Cys Xaa Xaa Xaa Xaa His Xaa Xaa Cys Xaa Xaa
            20                  25                  30

Xaa Xaa Xaa Cys Xaa Xaa
            35

( 2 ) INFORMATION FOR SEQ ID NO:12:

( i ) SEQUENCE CHARACTERISTICS:
    ( A ) LENGTH: 38 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:12:

Cys Xaa Xaa Cys Xaa Xaa Xaa Xaa Xaa Xaa Xaa Xaa Xaa Xaa Xaa
1               5                   10                  15

Xaa Ser Xaa Xaa Cys Xaa Xaa Xaa Xaa His Xaa Xaa Cys Xaa Xaa
            20                  25                  30

Xaa Xaa Xaa Cys Xaa Xaa
            35

( 2 ) INFORMATION FOR SEQ ID NO:13:

```
      ( i ) SEQUENCE CHARACTERISTICS:
            ( A ) LENGTH: 38 amino acids
            ( B ) TYPE: amino acid
            ( C ) STRANDEDNESS: single
            ( D ) TOPOLOGY: linear ( i i ) MOLECULE TYPE: protein ( x i ) SEQUENCE DESCRIPTION: SEQ ID NO:13:

Cys  Xaa  Xaa  Cys  Xaa  Xaa  Xaa  Xaa  Xaa  Xaa  Xaa  Xaa  Xaa  Xaa  Xaa  Xaa
1                   5                        10                            15

Xaa  Cys  Xaa  Xaa  Cys  Xaa  Xaa  Xaa  Xaa  Asp  Xaa  Xaa  Cys  Xaa  Xaa  Xaa
               20                       25                      30

Xaa  Xaa  Xaa  Cys  Xaa  Xaa
               35

( 2 ) INFORMATION FOR SEQ ID NO:14:

( i ) SEQUENCE CHARACTERISTICS:
            ( A ) LENGTH: 38 amino acids
            ( B ) TYPE: amino acid
            ( C ) STRANDEDNESS: single
            ( D ) TOPOLOGY: linear ( i i ) MOLECULE TYPE: protein ( x i ) SEQUENCE DESCRIPTION: SEQ ID NO:14:

Arg  Xaa  Xaa  Cys  Xaa  Xaa  Xaa  Xaa  Xaa  Xaa  Xaa  Xaa  Xaa  Xaa  Xaa  Xaa
1                   5                        10                            15

Xaa  Cys  Xaa  Xaa  Cys  Xaa  Xaa  Xaa  Xaa  His  Xaa  Xaa  Cys  Xaa  Xaa  Xaa
               20                       25                      30

Xaa  Xaa  Xaa  Cys  Xaa  Xaa
               35
```